US006485965B1

United States Patent
Klatzmann et al.

(10) Patent No.: US 6,485,965 B1
(45) Date of Patent: Nov. 26, 2002

(54) REPLICATING OR SEMI-REPLICATING VIRAL CONSTRUCTS, PREPARATION AND USES FOR GENE DELIVERY

(76) Inventors: David Klatzmann, 11 rue du Tage, Paris (FR), 75013; Arnaud Morel, 36 rue de Fontaines-Bât. A, Sevres (FR), 92310; Georg Holzer, 46 rue Poliveau, Paris (FR), 75005; Jean-Loup Salzmann, 70 rue Claude Bernard, Paris (FR)

(*) Notice: Subject to any disclaimer, the term of this patent is extended or adjusted under 35 U.S.C. 154(b) by 0 days.

(21) Appl. No.: 09/589,783

(22) Filed: Jun. 8, 2000

(Under 37 CFR 1.47)

(30) Foreign Application Priority Data

Jun. 9, 1999 (EP) .......................................... 99401391

(51) Int. Cl.[7] .......................... C12N 15/00; C12P 21/06; C07H 21/04
(52) U.S. Cl. ................. 435/320.1; 435/69.1; 536/23.72
(58) Field of Search ............................. 435/69.1, 320.1; 536/23.72

(56) References Cited

U.S. PATENT DOCUMENTS 5,858,740 A 1/1999 Zsebo ..................... 435/172.3
5,869,035 A 2/1999 Link et al. ................. 424/43.7

FOREIGN PATENT DOCUMENTS

WO 98 02529 1/1998

OTHER PUBLICATIONS

Petropoulos et al, "Replication–Competent Retrovirus Vectors for the Transfer and Expression of Gene Cassettes in Avian Cells," *Journal of Virology*, vol. 65, No. 7, 1991, pp. 3728–3737.

Greenhouse et al, "Helper–Independent Retrovirus Vectors with Rous–Associated Virus type O long Terminal Repeats", *Journal of Virology*, vol. 62, No. 12, pp. 4809–4812.

Gundlach et al, "Construction, Replication and Immunogenic Properties of a Simian Immunodeficiency Virus Expressing IL–2", *Journal of Virology*, vol. 3, No. 71, Mar. 1997, pp. 2225–2232.

Hoatlin et al, "Amplified and Tissue–Directed Expression of Retroviral Vectors Using Ping–Pong Techniques", *Journal of Molecular Medicine*, vol. 73, 1995, pp. 113–120.

*Primary Examiner*—Hankyel T. Park
(74) *Attorney, Agent, or Firm*—Nixon & Vanderhye P.C.

(57) ABSTRACT

The invention relates to the use of replicating or semi-replicating viral construct(s) for the preparation of a composition for gene delivery into cells in vivo, ex vivo or in vitro. The invention also relates to novel retroviral constructs, packaging cells and nucleic acids which can be used in methods of delivering polynucleotides to cells.

38 Claims, 13 Drawing Sheets

Figure 1:
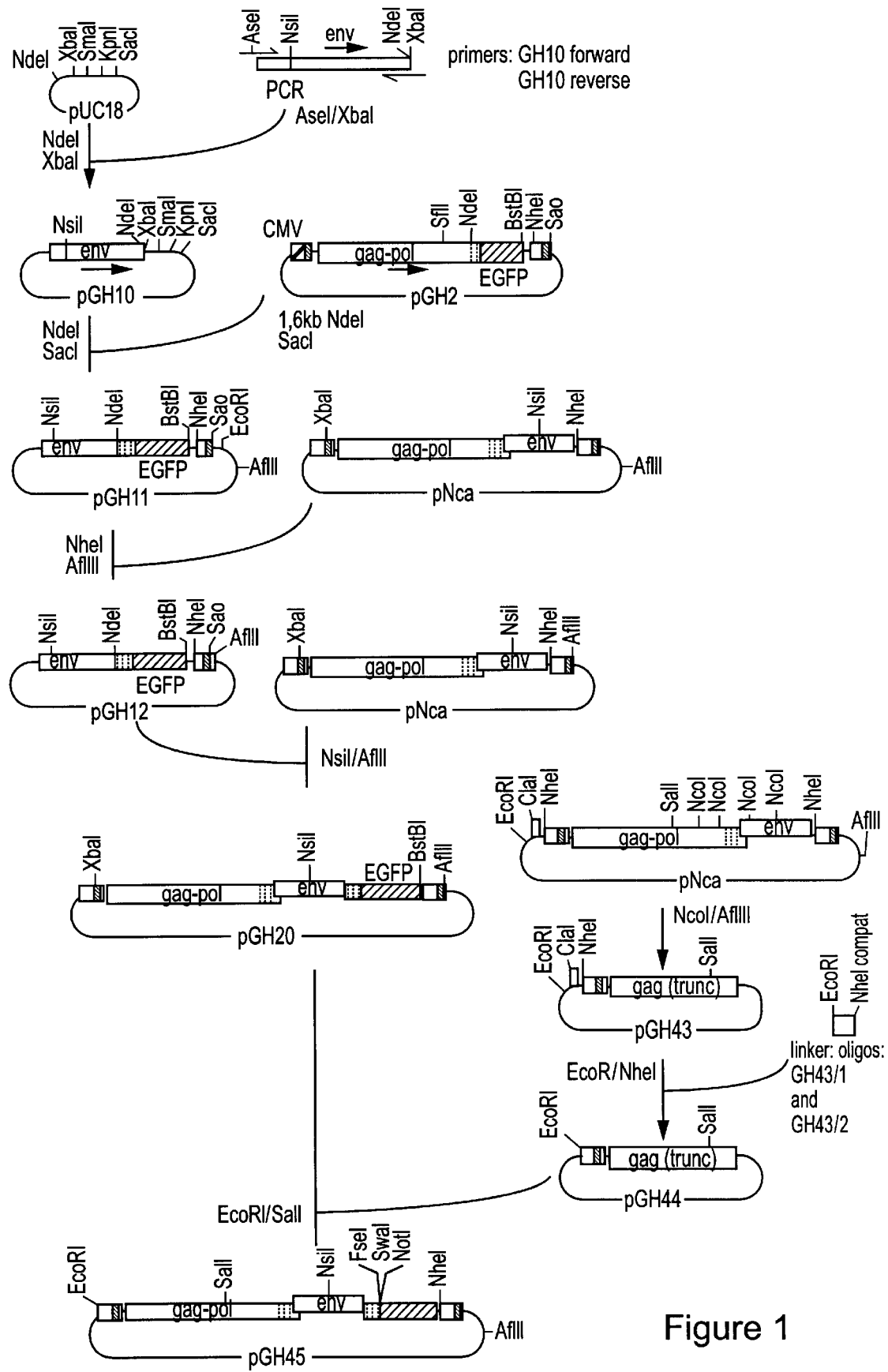

Figure 4A 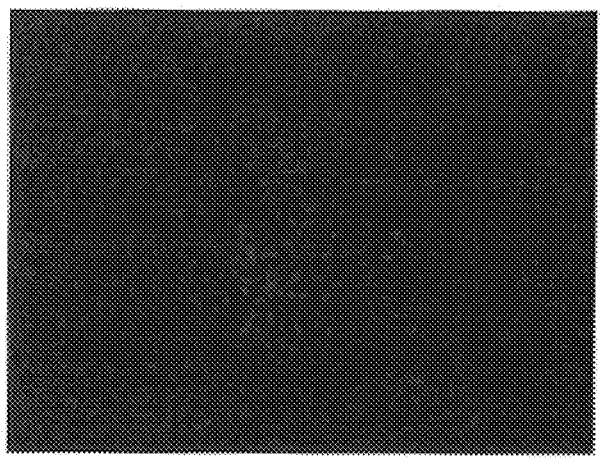 Figure 4B 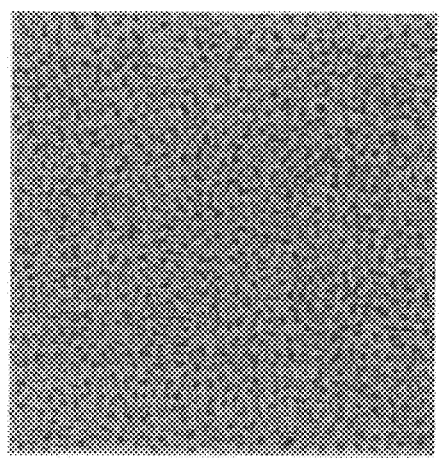
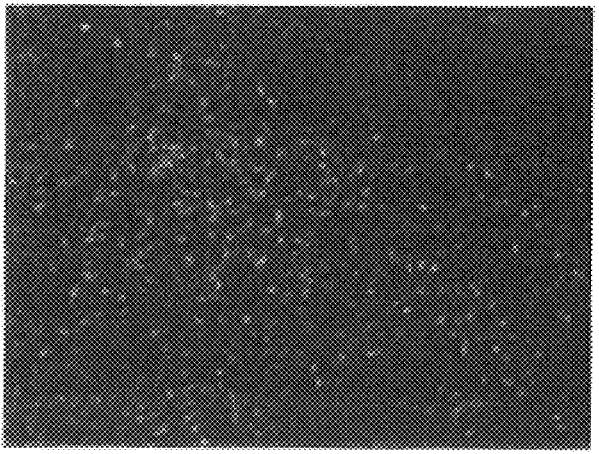 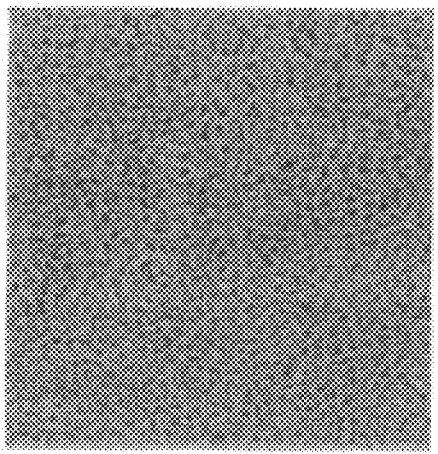

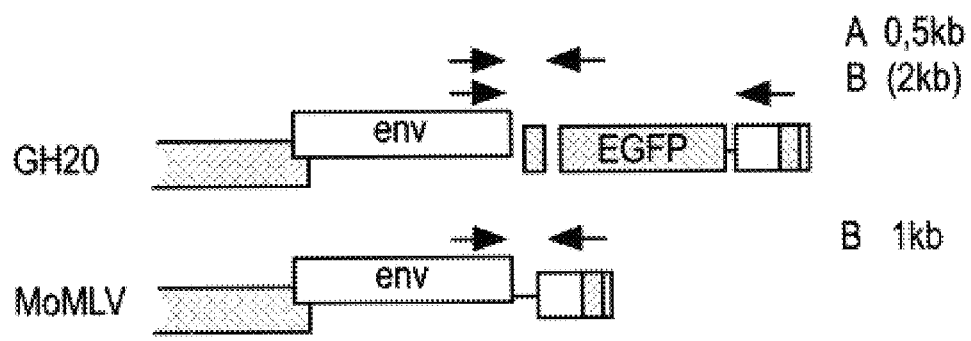
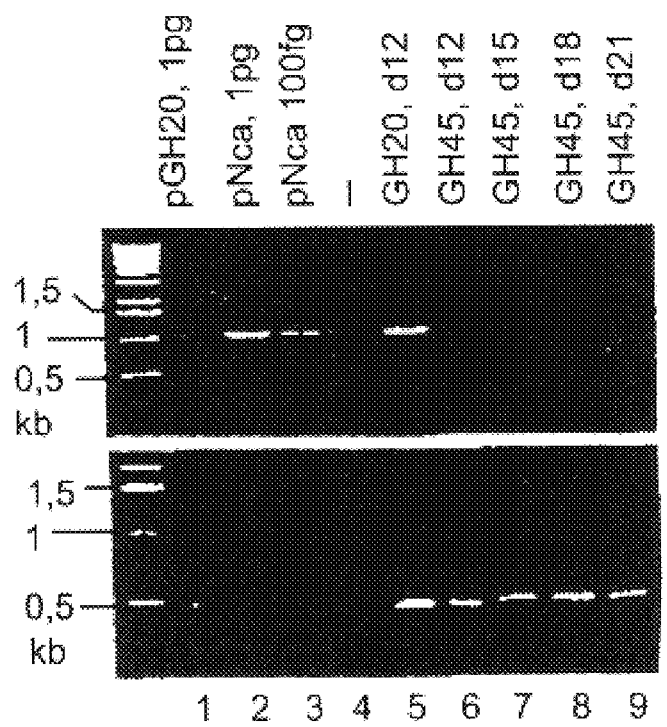
Figure 7B
Figure 7A

```
TCTAACCTAG AAAAGTCTCT CACTTCCCTG TCTGAAGTTG TCCTACAGAA TCGAAGGGGC CTAGACTTGT          70
TATTTCTAAA AGAAGGAGGG CTGTGTGCTG CTCTAAAAGA AGAATGTTGC TTCTATGCGG ACCACACAGG         140
ACTAGTGAGA GACAGCATGG CCAAATTGAG GTTAACAGA AGAGAGGCTT AATCAGAGAC AGAAACTGTT TGAGTCAACT  210
CAAGGATGGT TTGAGGGACT GTTAACAGA TCCCCTTGGT TTACCACCTT GATATCTACC ATTATGGGAC         280
CCCTCATTGT ACTCCTAATG ATTTTGCTCT TCGGACCCTG CATTCTTAAT CGATTAGTCC AATTTGTTAA         350
AGACAGGATA TCAGTGGTCC AGGCTCTAGT TTTGACTCAA CAATATCACC AGCTGAAGCC TATAGAGTAC         420
GAGCCATAGC ATATGA ATC TTATATGGGG CACCCCCGCC CCTTGTAAAC TTCCCTGACC CTGACATGAC         490
                  ↑                          ┌─────────┐
                  (I)                         CACTTACAG
                                              (III)
AAGAGTTACT AACAGCCCCT CTCTCCAAGC GCTCTCTACT TAGTCCAGCA CGAAGTCTGG                    560
AGACCCTCTGG CGGCAGCCTA CCAAGAACAA CTGGACCGAC CGGTGGTACC TCACCCTTAC CGAGTCGGCG         630
ACACAGTGTG GGTCCGCCGA CACCAGACTA AGAACCTAGA GCTTGGATAC AAAGGACCTT ACACAGTCCT         700
GCTGACCACC CCCACCGCCC TCAAGTAGA CGGCATCGCA GTTGGATAC ACGCCGCCA CGTGAAGGCT            770
GCCGACCCCG GGGGTGGACC ATCCCTCTAGA CTTAATTAA GGCCGGCCAT TTAAATAGCG GCCGCCACC↓         840
                                              ↓
                                              (IV)
┌──┐
TG TGAGCCAA GGGCGAGGAG CTGTTCACCG CCGGCGAGGG CATCCTGGTC GAGCTGGACG GCGACGTAAA         910
└──┘
 (V)
CGGCCACAAG TTCAGCGTGT CCGGCGAGGG CGAGGGCGAT GCCACCTACG GCAAGCTGAC CCTGAAGTTC         980
ATCTGCACCA CCGGCAAGCT GCCCGTGCCC TGGCCCACCC TCGTGACCAC CCTGACCTAC GGCGTGCAGT        1050
GCTTCAGCCG CTACCCCGAC CACATGAAGC AGCACGACTT CTTCAAGTCC
```

Figure 11

REPLICATING OR SEMI-REPLICATING VIRAL CONSTRUCTS, PREPARATION AND USES FOR GENE DELIVERY

This invention relates to compositions and methods for the delivery of nucleic acids into cells, in vitro, ex vivo or in vivo. More preferably, the invention relates to compositions and methods for the delivery of nucleic acids into cells using replicating or semi-replicating viral constructs, in particular replicating or semi-replicating retroviral constructs. The invention also relates to the preparation of said constructs, genetically modified cells which contain said constructs, such as packaging cells, as well as the use of these compositions and methods for the delivery of any selected polynucleotide to a cell, for experimental, prophylactic, therapeutic or diagnostic applications.

The delivery of nucleic acids to cells finds applications in various biotechnology and pharmacology areas, such as experimental research, clinical research, therapeutic or prophylactic treatment as well as diagnostic. Gene delivery in vitro can be used to produce recombinant proteins or viruses, for instance, as well as to produce stable recombinant cells for screening purposes. In vivo or ex vivo, gene delivery enables the construction of transgenic animals, the study of gene regulation, as well as therapeutic and/or prophylactic treatments of mammals, including human beings. In this regard, increasing amounts of animal and clinical trials have been reported in the literature, designed at delivering to subjects nucleic acids encoding therapeutic or antigenic polypeptides. These approaches use different gene transfer strategies, which comprise for instance the use of (i) viral vectors (or cells producing viral vectors), (ii) non-viral vectors (such as plasmids in combination with chemical agents or physical treatments), (iii) naked DNA or (iv) genetically modified cells which are grafted into the patient, optionally upon encapsulation to limit immune reaction.

The use of recombinant retroviruses is one of the most successful methods to introduce a nucleic acid into dividing cells, in vitro, in vivo or ex vivo. This gene transfer strategy has proven to be useful for both basic research and clinical applications. In this regard, in humans, much progress has been made for the transduction of hematopoietic progenitors (Nolta et al., Exp. Hematol. 20 (1992) 1065–1071), mature lymphocytes (Bunnell et al., Proc. Natl. Sci. USA 92 (1995) 7739–7743), tumor cells (Klatzmann et al. Hum. Gen. Ther. 9 (1998) 2595–2604; Caruso et al.; PNAS 90 (1993) 7024–7028), etc. Retroviruses have thus been validated as a gene delivery vehicle in vivo, in human subjects, for clinical applications (treatment of cancers, genetic diseases (e.g., ADA-deficiency, SCID), viral infections (e.g., HIV treatment), immune disorders (e.g., graft versus host disease, autoimmune diseases, etc.), etc.

Recombinant retroviruses which have been used in the art for gene delivery applications, are genetically modified to be rendered defective, i.e., to avoid replication of their genome and/or propagation upon infection of competent cells, in the absence of trans-complementing functions. In this respect, most recombinant retroviruses are created by replacing, in the recombinant genome, the viral genes gag, pol and env with a nucleic acid of interest. The recombinant, defective retroviruses are prepared in a so-called packaging cell, which produces the complementing functions encoded by gag, pol and env. Examples of such packaging cell lines are, for instance PA317 (Miller et Buttimore, Mol. Cell. Biol. 6 (1986) 2895), PsiCRIP (Danos et Mulligan, PNAS 85 (1988) 6460), or GP+EnvAm12 (Markowitz et al. Virology 167 (1988) p. 400). Other examples of retrovirus packaging cells have been described for instance in EP 243 204, WO89/07150, WO90/02806, U.S. Pat. No. 5,766,945, EP476,953, WO93/04167 and WO93/10218. The recombinant retroviruses produced in said cells are infectious, but cannot replicate themselves upon infection. In this regard, they are considered replication-defective. Such replication-defective recombinant retroviruses have been constructed using different types of retroviruses, including MOMLV (Moloney Murine Leukemia Virus) ALV, BLV, MMTV or RSV for instance, or using lentiviruses such as HIV, SIV or CAEV, for instance.

It is generally admitted that the gene delivery vectors should be as deficient as possible in order to avoid adverse effects upon administration in vivo. For this reasons, the retroviral vectors which have been used to date essentially lack all of the viral proteins gag, pol and env. The same concern also exists for all other types of viral vectors which are currently being used, such as adenoviral vectors, AAV, herpes virus vectors and the like. For instance, adenoviruses generally comprise a deletion of the E1 region at least, and current efforts are being made to produce "gutless" adenovectors, i.e., adenoviral vectors devoid of all viral coding sequences. Similarly, most recombinant MV vectors are devoid of the rep and cap coding regions.

However, while much progress has now been made in gene delivery vectors, there is still a need for alternative strategies which may increase gene transfer efficacy, gene expression stability and/or facilitate gene vector production, especially for industrial uses.

In Patent Application n° PCT/FR 95/00208, Applicants have disclosed a novel gene delivery concept. This concept comprises delivering to a cell, in vitro, ex vivo or in vivo, nucleic acid construct(s) comprising all of the genetic elements allowing said cell to produce a recombinant virus. This method therefore uses nucleic acids that create in situ recombinant virus producing cells. This method has been used for instance to deliver therapeutic or toxic genes in vivo, or to prepare vaccine compositions (see PCT/FR 97/00619 Noguiez-Hellin et al., PNAS 93 (1996) 4175–4180). This method offers several advantages over prior gene delivery vectors, and in particular it avoids the need for packaging cells, allows the use of recombinant plasmids to deliver the viral genes in vivo, provides efficient gene transfer in vivo, etc.

The instant invention now provides a novel approach for gene delivery into cells. This approach is based on the use of replicating or semi-replicating viral constructs to deliver genes in vitro, ex vivo or in vivo. In contrast with all prior existing methods, which where based on the use of replication defective viral constructs, the instant invention now stems from a new and original concept of using replicating or semi-replicating viral constructs, in particular replicating or semi-replicating retroviral constructs, for in vivo, ex vivo or in vitro delivery of polynucleotides. The instant invention shows that such constructs can be made in high quantity and quality and efficiently deliver and express any gene or nucleic acid of interest into cells in vitro, ex vivo or in vivo.

The instant invention therefore relates to methods and compositions for polynucleotide delivery into cells, in vitro, ex vivo or in vivo. More particularly, the invention relates to compositions comprising replicating viral constructs and their use in delivering polynucleotides to cells. The invention also relates to compositions comprising semi-replicating recombinant viral constructs and their use in delivering polynucleotides to cells. In other aspects, the invention also resides in packaging cells which produce replicating or semi-replicating recombinant viruses, and uses thereof.

The Use of Replicating Viral Constructs

As indicated above, in one embodiment, the invention resides in replicating viral constructs and uses thereof, in particular replicating retroviral constructs and uses thereof.

Numerous systems of retroviral vectors have been developed for gene delivery and gene therapy in the past decade. The main advantage of these systems is seen in the ability of these vectors to stably integrate into the hosts genome. In this regard, retroviruses such as MoMLV, selectively infect dividing cells, and are therefore considered as promising vectors for the transduction of proliferating cells (i.e., tumor cells, proliferating lymphocytes, etc.). Alternatively, retroviruses such as lentiviruses can infect also non-dividing cells and thus can be used as vectors to deliver genes to quiescent cells. For instance, MoMLV-derived retroviral vectors can be used to deliver genes to proliferating cells such as tumor cells or hematopoietic cells (in particular activated T lymphocytes), with the objective of destroying or modifying said cells. Lentivirus-derived vectors may be used to deliver polynucleotides to quiescent cells such as fibroblasts or muscle cells (in particular smooth or skeletal muscle), especially with the objective of raising an immune response against specific antigens or groups of antigens. Depending on the target cells or treatment conditions, these vectors, however, do not always provide sufficient transduction efficiency, and several approaches have been developed in order to address this aspect (strong promoters, targeted vectors, ex vivo gene transfer, etc.). The instant invention now provides a novel approach to improve the transduction efficiency of retroviral vectors. This approach is based on the use of replicating-viruses, which retain the ability to spread in the target cell population, tissue or organ.

Within the context of the present invention, the term "replicating" means that the construct(s) which are being used contain the genetic elements necessary for production of replicating recombinant viruses, i.e., recombinant viruses which are capable of replicating in the absence of any trans-complementing function, and therefore to spread in the target cell population, tissue or organ. These recombinant viruses are also termed replication-competent.

It is known that the genomic organization of retroviruses comprises essentially the following elements:

a LTR ("Long Terminal Repeat") region, located at each end of the genome, and functioning as the origin of replication and transcriptional promoter region. Each LTR region is composed essentially of three functional regions termed U3, R and U5, U5 and U3 being involved in the provirus integration, a packaging sequence ("Psi"), involved in the packaging of the proviral genome in the viral particle, three coding regions, designated gag, pol and env, coding the core proteins (gag), the enzymes (reverse transcriptase, protease, integrase) and the envelope glycoprotein (env).

In a general way, a replicating retroviral construct according to the present invention is therefore any construct (e.g., a nucleic acid, a plasmid, a virus) comprising at least functional gag, pol and env genes, as well as a polynucleotide to be delivered to cells. More specifically, the replicating retroviral construct according to the present invention comprises (i) functional gag, pol and env genes, (ii) a polynucleotide to be delivered to cells, (iii) a retroviral packaging sequence and (iv) at least one retroviral LTR sequence. These elements are also referred to in this application as the recombinant, replication-competent retroviral genome.

With regard to lentivirus, their genome further comprises additional coding or regulatory sequences, such as vif, vpr, vpu, vpx, rev, tat, and nef. A replicating lentivirus-type retroviral construct of the instant invention would thus preferably comprise elements (i)–(iv) listed above as well as (v) functional vif, vpr, vpu, vpx, rev, tat and nef sequences, or only a part thereof necessary for replication of the viral genome.

A replicating retroviral construct according to the present invention is therefore any construct (e.g., a nucleic acid, a plasmid, a virus) comprising at least a replication-competent retroviral genome, as defined above.

Within the context of the present invention, the expression "polynucleotide" designates any nucleic acid molecule whose delivery to a cell, culture, tissue, organ or organism is desired, as will be discussed below. This term may also encompass retroviral genes, such as retroviral envelope genes with fusogenic activity for instance. In this embodiment, the polynucleotide would represent the env gene.

More preferably, the replication-competent retroviral genome is a DNA or RNA molecule comprising, in the 5'→3' order:

(i) a retroviral 5' LTR region
(ii) a retroviral packaging sequence
(iii) functional gag, pol and env genes, and
(iv) a retroviral 3' LTR region,
said genome further comprising a selected polynucleotide inserted in a region of said genome which do not prevent the replication capacity of said genome.

Elements (i) to (iv) may be prepared by known techniques, starting from various materials and different types of retroviruses.

In particular, the functional gag and pol genes, the LTR sequence and the packaging region can derive from (be obtained from the genome of) retroviruses such as MOMLV (Moloney Murine Leukemia Virus) ALV, BLV, MMTV or RSV for instance, or from lentiviruses such as HIV, SIV or CAEV, for instance. These elements can be isolated and manipulated following techniques well known to the skilled artisan, or isolated from plasmids available in the art.

The functional env gene may encode an ecotropic (infectious in cells of the same species) or amphotropic (infectious in various species) envelope. Particular envelopes that can be used in the instant invention are, for instance, the envelope of the following viruses: 4070A (Ott et al., J. Virol. Vol. 64 (1990) p757–766), RD114, 10A1, VSV, VIH, rabies virus or GALV (Delassus S. et al., Virology 173 (1989) 205–213, which is fusogenic, or derivatives or other types disclosed in EP 99400964.5, which are fusogenic or non fusogenic). The envelope may also be of cellular origin, such as a membrane protein allowing targeting of the retrovirus to a selected ligand, such as a CD4 receptor for instance. Preferably, the envelope is a retroviral envelope having tropism for mammalian cells, more preferably human cells, in particular an amphotropic or retargeted envelope. GALV, 4070A or 10A1 represent preferred embodiment for the construction of replicating viruses of the instant invention. In this regard, as will be discussed below, the envelope gene or any variant thereof may also represent the polynucleotide of the vector constructs.

In addition, elements (i) and (iv) may be further modified in order to provide improved transduction efficiency, expression stability, or control over any spread of the retrovirus in vitro, ex vivo or in vivo. In particular, in preferred embodiments, modified envelope protein comprising a targeting moiety (a ligand, receptor, etc.) and/or a selected epitope, for instance, are being used. These modifications or variants will be disclosed in more detail below.

In a first embodiment of the present invention, the polynucleotide is inserted 3' of the envelope gene, preferably in the same transcriptional orientation as the env gene. In this respect, the invention now discloses a preferred and efficient way of producing a functional recombinant replication-competent genome as described above, comprising the creation of a second splice acceptor site within the viral genome, allowing translation of the polynucleotide from the transcriptional promoter contained in the LTR region. An example of such a construct is represented on FIG. 3. In a preferred embodiment, the invention therefore resides in a retroviral construct comprising a replication-competent retroviral genome comprising the following elements, in the 5'→3' order:

(i) a retroviral 5' LTR region
(ii) a retroviral packaging sequence
(iii) functional gag, pol and env genes,
(iv) a polynucleotide, and
(v) a retroviral 3' LTR region.
the retroviral genome further comprising a splice acceptor site between the env gene and the polynucleotide.

Where lentivirus-type retroviral constructs are used, elements (iii) above further comprises functional coding or regulatory sequences selected from vif, vpr, vpu, vpx, rev and tat, which are necessary for replication of such viruses.

This type of constructs has proven to be advantageous since it allows efficient expression of the polynucleotide, with no need for an additional (internal) promoter region. Furthermore, such an artificial construct, providing expression of the polynucleotide by alternative splicing, mimicks the natural expression mode in complex retroviruses. The inserted second acceptor splice site may duplicate the acceptor splice site already present in the retroviral construct, upstream of the env gene. This particular embodiment is illustrated in the Examples, wherein the created acceptor splice site comprises a fragment of a retroviral DNA of below 1 kb, comprising the MoMLV splice acceptor site. In a particular embodiment, the created splice acceptor site comprises a fragment of less than 1 kb, preferably less than 0,6 kb, of a sequence corresponding to the sequence of a retroviral acceptor splice site or a variant thereof, retaining the activity of a splice acceptor site. Variants may be tested for their activity in a retroviral construct of the instant invention, by verifying expression of the polynucleotide. In this respect, the structure and general properties of splice acceptor sites, in particular retroviral splice acceptor sites, are known to the skilled artisan. Splice acceptor sites are found in the genome of all retroviruses, between the pol and env genes. These splice acceptor sites regulate transcription of the env gene from the 5'-LTR. Any splice acceptor site can therefore be used in the instant invention, such as a DNA fragment of a different size containing the splice acceptor, a synthetic sequence, or a corresponding region from another retrovirus. In a preferred embodiment, the splice acceptor site comprises all or a portion of SEQ ID NO:6, or a variant thereof. More preferably, the splice acceptor site is a nucleic acid fragment comprising the sequence of position 437 to position 802 of SEQ ID NO: 6, or a variant thereof. Even more preferably, the inserted nucleic acid comprises the sequence of position 532 to position 540 of SEQ ID NO: 6, or a variant thereof. In preferred embodiments the inserted nucleic acid comprising the splice acceptor site comprises less than about 1,5 kb, even more preferably, about 1 kb or less.

Furthermore, as another aspect of this invention, the duplication of a retroviral (e.g., the MoMLV) splice acceptor region results in a tandem repeat, flanking the env gene (FIG. 3). Deletion of genomic sequences due to repeated sequences in the retroviral genome has been described previously. Altering the size of the repeated regions within such a replicated vector is proposed as a means to control its virulence by targeted destabilization of the viral env gene without affecting the expression of the gene of interest. In this regard, this embodiment therefore creates an attenuated replication-competent retrovirus (Sorge et al., J. Mol. Appl. Genet. 1 (1982) 547; Hugues et al., Virology 136 (1984) 89).

Alternatively, because deletion of the polynucleotide from the replicating genome may also be observed, the invention also proposes to use any such deletion event as a further means to control viral spread. In particular, by rendering viral replication dependent from the presence of the polynucleotide, it is possible to take advantage of any possible deletion event affecting the polynucleotide. In a more particular embodiment, the replicating viral construct comprises a modified LTR region, which is active in the presence of a polypeptide encoded by (i) the viral construct itself or (ii) another viral construct.

More particularly, a specific object of this invention resides in a replicating viral construct, wherein said viral construct comprises a modified LTR region which is active in the presence of an activating polypeptide, and wherein said viral construct comprises a polynucleotide encoding said activating polypeptide. Even more preferably, the activating polypeptide is encoded by the same polynucleotide that encodes the product whose delivery is sought. The two polypeptides may be produced as a single, fusion molecule, that may be cleaved within the cells upon expression, for instance by digestion of a cleaving site introduced between said two polypeptides. Alternatively, the two polypeptides may be produced as two separate molecules, the respective coding nucleic acids being fused by means of IRES for instance. In these embodiments, any deletion event of the polynucleotide creates a replication-defective viral construct and thus avoids dissemination thereof. In a further preferred embodiment, the activating polypeptide is expressed from the viral construct under the control of a regulated or (tissue or cell) selective promoter, to further control viral replication. Examples of such promoters are described later in this application.

The activating polypeptide may be any transactivator molecule, such as a tetracycline responsive trans-activator or the HIV Tat/tar system, or any other transcription activating molecule, preferably of non-human origin, to ensure higher selectivity of the system. The modified LTR may comprise the operating sequences to which the transactivator binds, thereby activating expression from the LTR. Said operating sequence may for instance be inserted in replacement of all or part of the U3 region of the LTR. The operating sequences may be inserted in one or several tandem copies, for instance between 1–8 copies, more preferably 1 to 5. The tetracycline operator sequences (TetOp) can be prepared by the skilled artisan using conventional techniques. In this regard, another aspect of the present invention also resides in a modified retroviral LTR, wherein said LTR comprises a transcription activator operator sequence in replacement of all or part of the U3 region.

As will be further described below, the activating polypeptide may also be expressed by a separate viral construct, in particular in the case of semi-replicating viral constructs. In that situation, not only are the viral constructs dependent from each other with regard to the nature of the proteins produced, but they are also dependent for activating expression thereof.

While insertion of the polynucleotide 3' of the env nucleic acid encoding region as described above represents a preferred embodiment of this invention, it should be understood that other insertion sites or strategies can be used. More particularly, within the replicating viral constructs of the present invention, the polynucleotide may also be inserted:

5' of the env gene, the second splice acceptor site being used to regulate env protein expression, or 3' of the envelope gene, as a bicistronic unit therewith. More particularly, an IRES sequence (Internal Ribosome Entry Site) can be inserted between the env gene and the polynucleotide, to ensure co-expression of said region from the 5'-LTR, 3' of the envelope gene, but in the opposite transcriptional orientation. In this embodiment, transcription of the polynucleotide is controlled by an internal promoter region contained in the polynucleotide which, as described later, may be a regulated and/or cell or tissue selective promoter.

Although less preferred, the polynucleotide may also be present into other locations of the viral genome, such as for instance in the U3 region of the LTR sequence.

Preferred replicating viral constructs or genomes of this invention, and, in particular, preferred retroviral constructs or genomes of this invention comprising (i) functional gag, pol and env genes, (ii) a polynucleotide to be delivered to cells, (iii) a retroviral packaging sequence and (iv) at least one retroviral LTR sequence, are further characterized in that:

they encode a modified envelope protein having a modified host range (i.e., retargeted envelope), and/or they encode a modified envelope protein comprising a selected epitope, and/or they comprise a modified LTR sequence that is active in the presence of an activating polypeptide, and/or the polynucleotide encodes αGal4, and/or the polynucleotide encodes an immunogenic polypeptide or a cytokine, and/or the polynucleotide encodes a (conditionally) toxic molecule, and/or the polynucleotide comprises a regulated or selective promoter.

These characteristics can be present within the viral constructs of this invention as any combination thereof. Preferably, at least one or two of said features are present within the constructs.

As indicated above, the replicating (retro)viral constructs of the present invention can be a nucleic acid, a plasmid, a vector or a virus, for instance, comprising the above-disclosed genome.

In one embodiment of the present invention, the retroviral construct is a retroviral vector or plasmid, i.e., a linear or circular nucleic acid (RNA or DNA) comprising a recombinant replication-competent (retro)viral genome as defined above.

Accordingly, in one aspect, the invention resides in a plasmid comprising a recombinant replication-competent retroviral genome as defined above, as well as in any composition comprising such a plasmid. The invention also resides in a method for delivering a polynucleotide to cells, comprising contacting said cells (culture, tissue, organ, etc.) in vitro, ex vivo or in vivo with said plasmid or composition.

This embodiment is advantageous since plasmid or vector constructions, manipulations and production can be performed in any suitable host cell, according to conventional recombinant DNA techniques. For instance, in a particular embodiment of the present invention, the retroviral construct is a plasmid comprising a recombinant, replication-competent retroviral genome as defined above, and an origin of replication functional in a host cell such as a prokaryotic or eukaryotic host cell. The plasmid can therefore be prepared in any convenient host cells such as bacteria (e.g., E.coli) or yeast cells (e.g., saccharomyces, kluyveromyces, etc.), and there is no requirement for a stable packaging cell line, a confined environment, complex purification methods, etc. In a particular aspect of the invention, the plasmid may further comprise a marker gene, further facilitating the construction, manipulation and production thereof in vitro.

Another advantage of this embodiment of the present invention is that high levels of plasmid transduction are not required to obtain efficient gene delivery. Indeed, upon contacting with the cell, culture, tissue, organ, or the like, the plasmid or vector penetrates into the cells and allows the recombinant retroviral genome to be replicated (usually after integration thereof into the host genome). The replicated recombinant retroviral genome is then packaged into retroviral particles, which are formed by assembly of the core and envelope proteins expressed from the functional gag and env genes, and subsequently released outside of the transduced cells. Considering the replication and packaging efficiency of retroviruses, this method allows the production of large amounts of recombinant replication-competent retroviral particles from one plasmid or vector incorporated into one cell. In this regard, the examples which follow clearly demonstrate efficient propagation of the recombinant retrovirus. Accordingly, even where the initial contacting step is not improved or optimized, this method allows the production of large amounts of infectious, recombinant, replication-competent retroviral particles which can spread and infect surrounding cells and allow high polynucleotide transfer efficiency, in vitro, ex vivo or in vivo.

The invention therefore also resides in methods of delivering a polynucleotide to a cell, in vitro, ex vivo or in vivo, comprising contacting said cell with a plasmid or composition as described above. The invention also resides in the use of a plasmid or composition as described above for the preparation of a composition for delivering a polynucleotide to a cell, in vitro, ex vivo or in vivo.

In a particular embodiment, the contacting step can be performed in the presence of any agent or treatment known to facilitate cell transduction. In this regard, various transfecting agents have been reported in the literature, such as liposomes, cationic lipids, peptides, polymers, etc., as well as physical treatments such as electrical field, gene gun, balistic methods, and the like. Any such treatment and/or method can be applied to the initial contacting step in order to further increase the transduction of the plasmid, if appropriate. Alternatively, the contacting step can be performed with naked DNA plasmid compositions, especially for intramuscular gene delivery. Obviously, any other method, agent, treatment or condition known to improve the contacting step can be used in performing the instant method.

In particular embodiments, the contacting step can be performed by liposome-, cationic lipid-, polymer- or peptide-mediated transfection.

In another particular variant of the invention, a replication-defective virus is used to deliver the above vector/plasmid or, more generally, the replicating viral genome, to the cells. In this regard, the retroviral genome (or vector/plasmid) can be inserted in a defective adenoviral or MV vector, an herpes amplicon, a vaccinia virus vector or the like. The initial contacting step thus involves the infection of the cell, culture, tissue or organ with the corresponding virus (e.g., adenoviruses, MVs, HSV, vaccinia) for instance.

According to another embodiment of the present invention, the replicating retroviral construct is a recombinant retrovirus comprising the recombinant, replication-competent retroviral genome as defined above.

Another object of the instant invention therefore resides in a replicating retrovirus comprising a recombinant, replication-competent retroviral genome as defined above, as well as in any composition comprising such a retrovirus, and uses thereof. More preferably, in the replicating genome, the polynucleotide is inserted outside of the LTR sequences, preferably 3' of the env-coding region, even more preferably, downstream of a splice acceptor site.

In another preferred embodiment, the replicating retroviral gene encodes a modified env glycoprotein, e.g., a retargeted env protein with modified tropism, in particular allowing preferential infection of selected cell population(s), tissue(s) or organ(s), and/or an immunogenic env protein (containing a selected epitope) as will be discussed in more detail below.

Obviously, in a particular embodiment, the replicating retroviral genome may combine the above two features, as well as others which will be described later in this application.

If desired, the recombinant retrovirus comprising the recombinant, replication-competent retroviral genome can be produced in vitro, either by transient transfection of a competent cell with the retroviral construct, or from a corresponding stable packaging cell line, i.e., a population of cells comprising, integrated into their genome the replication-competent retroviral genome as defined above.

In vitro production by transient transfection can be accomplished as described above, by contacting a competent cell population with a retroviral vector or plasmid comprising a replication-competent retroviral genome, followed by recovery of the recombinant retroviruses produced. Competent cells can be for instance any mammalian or insect cells, which can be grown in culture, do not exhibit known significant pathogenic activity, and can replicate a retroviral genome. The cell can be established as an immortalized cell line, or a culture of primary cells. More preferably, the competent cell is a mammalian cell, such as a rodent cell, a primate cell or a human cell. Specific examples include, fibroblasts (such as NIH 3T3), retinoblasts, kidney cells (e.g., 293 cells) and the like. Other examples of competent cells or cell lines have been described in EP 243 204, WO 89/07150, WO 90/02806 or WO 93/10218 for instance.

Alternatively, as mentioned above, a packaging cell producing a recombinant replication-competent retrovirus of the present invention can be prepared. For this purpose, a population of competent cells established as a cell line is contacted with a retroviral vector or plasmid comprising a replication-competent retroviral genome and, optionally, a marker gene. Clones of competent cells having stably integrated the retroviral genome can be selected and subcultured. Cell banks can then be prepared, including master cell banks, controlled by various techniques such as PCR for stable integration of the recombinant retroviral genome, and stored under appropriate condition. Within the context of the present invention, stable integration of the genome means that the recombinant retroviral genome remains integrated within the host cell genome over at least 20 generations (i.e., over 20 cell divisions). Production from such packaging cells comprises (i) culturing the cells in appropriate medium and conditions to allow replication of the genome, expression of the core and envelope proteins, packaging and release of the retroviruses, (ii) followed by recovering of the viruses produced.

In this regard, another object of the present invention resides in a retroviral packaging cell, wherein said packaging cell comprises, integrated into its genome, a recombinant replication-competent retroviral genome, as described above. As discussed before, previously described retrovirus packaging cells produce replication-defective retroviruses. In contrast, the packaging cells as presently claimed allow the production of replicating retroviruses.

Where recombinant viruses are being used, the contacting between the population of cells and the recombinant retrovirus may be accomplished in vitro, ex vivo or in vivo by incubating the cells in the presence of a suspension of the retroviruses. The suspension can be a supernatant of a packaging cell culture producing the virus, or a dilution or concentrate thereof. The suspension can also be a partially purified supernatant, enriched for the viruses, obtained according to known methods (i.e., gradient centrifugation, chromatography or the like). The incubation is generally performed with a suspension of retroviruses comprising between $10^4$ and $10^7$, more preferably between $10^4$ and $10^6$ viral particles approximately. It should be understood that the precise amount of viruses per cell used in the method can be adapted by the skilled artisan without undue experimentation. Contacting may also be obtained by cocultivating the target cells, tissue, organs, etc. with packaging cells as described above (for in vitro or ex vivo uses) or by grafting said packaging cells in vivo, as described below.

As illustrated in the examples, the use of (securized) replicating viral constructs according to the present invention provides a very efficient way of delivering nucleic acids to cells, in vitro, ex vivo or in vivo, in particular to proliferating cells, more preferably to tumor cells.

The use of Semi-replicating Viruses

According to another embodiment, the invention resides in the use of semi-replicating viral constructs, in particular semi-replicating retroviral constructs.

The term "semi-replicating viral constructs" designates a combination of viral constructs (to be used simultaneously or sequentially) which transcomplement each other to allow replication thereof in competent cells (and/or which are interdependent for replication and/or gene expression).

More particularly, the invention resides in a composition comprising at least two retroviral constructs, for simultaneous, separated or sequential use, wherein said at least two retroviral constructs transcomplement each other when present in a cell, at least one of said retroviral constructs comprising a polynucleotide of interest.

According to a first variant, the composition of this invention comprises (i) a replicating retroviral construct and (ii) a replication-defective retroviral construct lacking a functional gag and/or pol and/or env gene, one or both of said retroviral constructs comprising a polynucleotide of interest.

In this particular variant, the replication-defective viral construct is transcomplemented by the replicating viral construct, replication and propagation of the replication-defective construct being obtained in the presence of the replicating construct. The inventors have now surprisingly shown that, in such a situation, the replication defective construct replicates with a very high efficiency, i.e., similar to or higher than that of the replicating construct. This appears to be due to a negative effect of the env gene on encapsidation of the retroviral genome. This embodiment is thus advantageous in that a therapeutic polypeptide may be expressed from the defective construct. Alternatively, the therapeutic polypeptide may be expressed from the replicating construct, or from both. In a preferred embodiment, the replicating viral construct is securized as described above, to control spread or replication or expression thereof. In addition, replication or gene expression from the replicating viral construct is even more preferably dependent from the presence of the defective viral construct, so that both constructs depend from each other for replication and/or gene expression, thereby ensuring high expression levels, high transduction efficiency, and control over viral spread. Such inter-dependency may be achieved by rendering gene expression or replication in the replicating construct dependent from an activating polypeptide expressed by the relication-defective viral construct. Further control over viral spread may be achieved by additional methods as described later in this application.

In a preferred embodiment, this invention relates to a composition comprising, for simultaneous, separate or sequential use, (i) a securized replicating retroviral construct and (ii) a replication-defective retroviral construct lacking functional gag, pol and/or env genes, one or both retroviral constructs comprising a polynucleotide.

In a particular embodiment, the replication-defective viral construct comprises all or part of gag and pol genes and lack a functional env gene, preferably through deletion of all or part thereof, more preferably all of env coding sequences.

In an other particular embodiment, the replication-defective viral construct lack functional gag, pol and env genes, preferably through deletion of all or part thereof, more preferably all of their coding sequences.

In a preferred embodiment, the securized replicating viral construct is a replicating viral construct comprising a modified LTR region which is active in the presence of an activating polypeptide encoded by the replication-defective viral construct.

Alternatively, or in addition, the securized replicating viral construct may comprise a modified envelope and/or encode a polypeptide selected from cytokines, toxic molecules (e.g. thymidine kinase) and αGAL4.

Furthermore, in performing these embodiments of the invention, it may be advantageous that the at least the two viruses essentially lack significant homology or overlapping region, to avoid recombination events therebetween. In particular, while homology within LTR or packaging sequences are tolerated, it is preferred that the replication-defective viral construct lacks essentially all of the pol and env genes, even more preferably all of the pol and env genes and at least a portion of the gag gene.

It should be understood that the present invention more generally extends to any combination of a replicating viral construct and a replication-defective viral construct for simultaneous, separate or sequential use for gene delivery in vitro, ex vivo or in vivo.

In this regard, this invention also relates to methods of delivering a polynucleotide to cells, in vitro, ex vivo or in vivo, comprising simultaneously or separately or sequentially contacting the cells with at least (i) a replicating retroviral construct and (ii) a replication-defective retroviral construct lacking functional gag, pol and/or env gene, at least one of said retroviral constructs comprising a polynucleotide.

In another variant, each of the at least two trans-complementing retroviral constructs lacks at least one viral gene selected from gag, pol and env.

In this regard, a specific embodiment of this invention resides in a composition comprising at least two semi-replicating retroviral constructs, for simultaneous, separated or sequential use, wherein said at least two semi-replicating retroviral constructs transcomplement each other when present in a cell and comprise a polynucleotide. Preferably, said two or more retroviral constructs encode or exhibit different envelope glycoproteins.

In particular, semi-replicating viral constructs comprise, in a preferred embodiment, at least 2 different retroviral constructs having the following characteristics:

each of said retroviral constructs comprises a recombinant retroviral genome, wherein said genome (i) lacks at least one viral gene or regulatory sequence (selected for instance from gag, pol and env) and (ii) comprises a polynucleotide, said recombinant retroviral genomes of said retroviral constructs trans-complementing each other when present in a cell.

More preferably, the 2 or more different retroviral constructs are further characterized in that there is no significant sequence overlap between the viral genes gag, pol and env contained in each recombinant retroviral genome.

As will be described below in more details, the use of such semi-replicating viruses is advantageous and provides efficient delivery and spread of a polynucleotide to cells, in vitro, ex vivo or in vivo. Again, and in contrast with all previous strategies to modify viral genomes, which are directed at producing defective virus preparations, free of replication-competent viruses, and avoiding or minimizing the risks and/or consequences of recombination/complementation events, the invention resides in the use of semi-replicating viral constructs (which trans-complement each other) and ensure more efficient delivery and spread of a polynucleotide within the cells, tissue, organ, etc. This new concept of trans-complementing retroviruses can be implemented in various different ways and according to many different embodiments.

In a first preferred embodiment of the invention, two semi-replicating retroviral constructs are used, having the following properties:

the first semi-replicating retroviral construct comprises a first recombinant retroviral genome which (i) lacks an env gene and (ii) comprises a first polynucleotide, the second semi-replicating retroviral construct comprises a second recombinant retroviral genome which (i) lacks gag and pol genes and (ii) comprises a second polynucleotide, said first and second retroviral genomes trans-complementing each other when present in a cell.

More preferably, in the above two constructs the env gene present in the second retroviral genome lacks significant sequence overlap with the gag and pol genes present in the first retroviral genome.

This system can be extended to lentivirus-type retroviral constructs as disclosed before, with further transcomplementations in additional coding or regulatory sequences.

Also, the first and second polynucleotides present in the first and second retroviral genomes can encode the same (or essentially similar) products or, alternatively, different products (i.e., a cytokine and an immunigenic polypeptide, etc).

In an other preferred embodiment of the invention, three semi-replicating retroviral constructs are used, having the following properties:

the first semi-replicating retroviral construct comprises a first recombinant retroviral genome which (i) lacks an env gene and (ii) comprises a first polynucleotide, the second semi-replicating retroviral construct comprises a second recombinant retroviral genome which (i) lacks gag and pol genes and (ii) comprises a second polynucleotide, the third semi-replicating retroviral construct comprises a third recombinant retroviral genome which (i) lacks gag and pol genes, (ii) comprises an env gene which is different from the env gene of the second recombinant retroviral genome, and (iii) comprises a third polynucleotide, said first, second and third retroviral genomes transcomplementing each other when present in a cell.

More preferably, in the above three constructs:

the env genes present in the second and third retroviral genomes lack significant sequence overlap with the gag and pol genes present in the first retroviral genome.

Again, this system can be extended to lentivirus-type retroviral constructs as disclosed before, with further transcomplementations in additional coding or regulatory sequences In a particular and preferred embodiment, the first (or gp, for "gag-pol") retroviral genome comprises a truncated retroviral pol DNA. More particularly, the gp retroviral genome comprises a truncated retroviral pol DNA which lacks any overlapping sequence with the env coding region contained in the second and third retroviral genome. The use of such truncated pol DNA increases the safety of the delivery system. Indeed, in a retroviral genome, the pol and env genes overlap. These overlapping sequences can allow some recombination event to take place, which may affect the genetic stability of the constructs and the quality of the recombinant retroviruses. The inventors have shown that it is possible to prepare a truncated retroviral pol DNA, that lacks or has reduced overlapping sequence with env, and still remains biologically active (U.S. patent application Ser. No. 09/113,280). In a preferred embodiment, the gp retroviral construct of the present invention therefore comprise a nucleic acid coding for a biologically active retroviral POL protein lacking between 3 to 50 amino acid residues at the C-terminal end, at least. Preferably, the nucleic acid lacks 80% at least of the overlapping sequences with the env coding region, more preferably at least 90%. An example of the 3' end of such a nucleic acid is GGACCATCCTCTAG (SEQ ID NO: 1). Any variant of pol with modified residues that still retains the biological activity of POL can obviously be used, including truncated POL encoding nucleic acids prepared from MoMLV, MMTV or RSV retroviruses. Such variants also include mutants of the above sequence comprising preferably less than 10%, more preferably less than 5%, advantageously less than 3% of modified amino acids.

These semi-replicating retroviral constructs can be any plasmid, vector, nucleic acid, virus or producing or packaging cell as described for the replicating viruses, and they can be prepared essentially according to conventional techniques known in the art.

In a preferred embodiment, the semi-replicating retroviral constructs are semi-replicating retroviruses which comprise the above-disclosed genomes.

In this respect, the invention relates to composition comprising at least two semi-replicating retroviruses (in particular two MoMLV-derived retroviruses), for simultaneous, separated or sequential use, said semi-replicating retroviruses (i) lacking at least one viral gene selected from gag, pol and env, (ii) transcomplementing each other when present in a cell, (iii) comprising a polynucleotide and (iv) having a different envelope glycoprotein.

The invention also relates to compositions comprising at least three semi-replicating retroviruses (in particular three MoMLV-derived retroviruses), for simultaneous, separated or sequential use, said semi-replicating retroviruses (i) lacking at least one viral gene selected from gag, pol and env, (ii) transcomplementing each other when present in a cell, (iii) comprising a polynucleotide and (iv) having a different envelope glycoprotein.

In this respect, a first preferred variant of this invention is a composition comprising:

(a) a first retrovirus comprising a first recombinant retroviral genome which (i) lacks an env gene and (ii) comprises a first polynucleotide, (b) a second retrovirus comprising a second recombinant retroviral genome which (i) lacks gag pol genes and (ii) comprises a second polynucleotide, said first and second retroviruses transcomplementing each other when present in a cell and having different envelope glycoproteins, said first and second viruses being used simultaneously or sequentially. In performing the invention, it is important that the two (or more) viruses which are used express a different envelope glycoprotein. Indeed, using the same envelope protein would significantly impair co-infection of a cell with both (or more) types of retroviruses. The envelopes may be selected from any known envelope as described above, including modified and/or retargeted envelopes.

The semi-replicating retroviruses may be produced using corresponding packaging cells, i.e., retrovirus packaging cells having stably integrated semi-replicating retroviral genomes. In this regard, an object of the instant invention resides in a retrovirus packaging cell, comprising, integrated into its genome, a recombinant retroviral genome comprising at least one functional retroviral gene selected from gag, pol and env. Indeed, the invention describes for the first time retrovirus packaging cells which produce retroviruses containing functional viral genes.

In a particular embodiment, the retroviral genome is a replicating retroviral genome, i.e., a retroviral genome as defined above comprising functional gag, pol and env genes as well as a selected polynucleotide.

According to another embodiment, the retroviral genome is a semi-replicating retroviral genome which comprises functional gag and pol genes and lacks an env gene. More preferably, the semi-replicating retroviral genome further comprises a selected polynucleotide. In a more preferred embodiment, the semi-replicating retroviral genome comprises a truncated pol gene lacking significant sequence overlap with retroviral env genes.

According to another embodiment, the retroviral genome is a semi-replicating retroviral genome which comprises a functional env gene and lacks gag and pol genes. More preferably, the semi-replicating retroviral genome further comprises a selected polynucleotide.

In a particular embodiment, the invention resides in a retrovirus packaging cell comprising a first and a second retroviral genome, wherein said first retroviral genome is a semi-replicating retroviral genome which comprises functional gag and pol genes and lacks an env gene and said second retroviral genome is a semi-replicating retroviral genome which comprises functional env gene and lacks gag and pol genes.

The above packaging cells can be prepared from any competent cell as defined above. These cells are preferably mammalian cells, in particular rodent or human cells.

The invention also resides in compositions comprising a retrovirus packaging cell as disclosed above. Indeed, these packaging cells can be used for producing replicating or semi-replicating retroviruses in vitro as well as in vivo, upon grafting in a subject. Accordingly, the invention relates to a method of delivery a polynucleotide to a cell, tissue or organ, in vitro, ex vivo or in vivo, comprising contacting said cell tissue or organ with a composition of semi-replicating retroviruses as described above, or a composition of packaging or s producing cells. Contacting with semi-replicating retroviruses. For in vivo uses, administration can be made by different routes, such as intratumoral, intramuscular, intravenous, intraperitonal, etc. when packaging or producing cells are used, grafting can be accomplished according to various techniques which have been used in clinical trials (injection, coating, etc.) in different areas (intratumoral, cutaneous, intramuscular, etc.). The amount of cells to be grafted can be adapted by the skilled artisan depending on the polynucleotide, subject, etc. The skilled artisan may easily uses the information disclosed in Klatzmann et al. (Hum. Gen. Ther. 9 (1998) 2595–2604) which is incorporated therein by reference.

In another preferred embodiment, the compositions and methods use DNA constructs (such as plasmids or linear DNA constructs) to deliver the semi-replicating genomes. In a more preferred embodiment, the semi-replicating retroviral constructs are nucleic acid constructs (such as plasmids) with the following characteristics:

(a) a first nucleic acid construct comprising, in two distinct regions (i) a first semi-replicating retroviral genome comprising functional gag and pol genes, lacking an env gene, and comprising a first polynucleotide ; and (ii) a nucleic acid region encoding a first env glycoprotein; and (b) a second nucleic acid construct comprising, in two distinct regions (i) a second semi-replicating retroviral genome comprising a functional env gene encoding a second env glycoprotein distinct from the first env glycoprotein, lacking gag and pol genes, and comprising a second polynucleotide ; and (ii) a nucleic acid region encoding functional gag and pol proteins. Obviously, regions (i) and (ii) of each nucleic acids (a) and (b) could be used as separate entities, as shown on FIG. 8. Preferably, however, these 4 entities are used in the form of two plasmids (or plasmoviruses). Each plasmid (or plasmovirus), when introduced into a cell, produces a recombinant semi-replicating retrovirus comprising the recombinant genome and expressing the corresponding envelope glycoprotein. Said plasmids can be used in vitro, to produce the retroviruses, or to deliver the polynucleotide. The plasmids can also be used in vivo, to deliver the polynucleotide to target cells.

Indeed, upon transfection of cells in vivo, each plasmid will induce replication and production of semi-replicating viruses. Following production of said viruses, every cell co-infected with both viruses will allow their replication, thereby facilitating further propagation of the polynucleotide. Because of this transcomplementing effect, this system is also termed "Ying-yang".

Of course, the system can also be extended to more than two retroviral constructs. For instance, a third plasmid comprising a third semi replicating retroviral genome and a complementing gene may also be used, in combination with the above two constructs.

In order to avoid or limit recombination events, it is preferred that the gag-pol and env genes present in the semi-replicating retroviral genomes lack significant sequence overlap. In this regard, a truncated pol gene as described above can be used advantageously.

Furthermore, the first and second polynucleotides may encode essentially the same product, in a particular embodiment, they encode different products. In this respect, one of the polynucleotides may encode a marker product or a toxic product (i.e., suitable to arrest the procedure if necessary or desirable).

As explained before, these nucleic acid constructs (e.g., plasmids) can be prepared by conventional techniques, as disclosed in U.S. Ser. No. 08/696,941 for instance. Preferably, all the viral constructs used (whether plasmids, viruses or any other molecule) are designed to express envelope glycoproteins with affinity for human cells. In this regard, preferred envelopes are 4070A, RD114, 10A1, GALV, VSV, VIH and derivatives thereof, in particular retargeted derivatives thereof.

These semi-replicating viral constructs can be used in many different ways.

Figure 9:
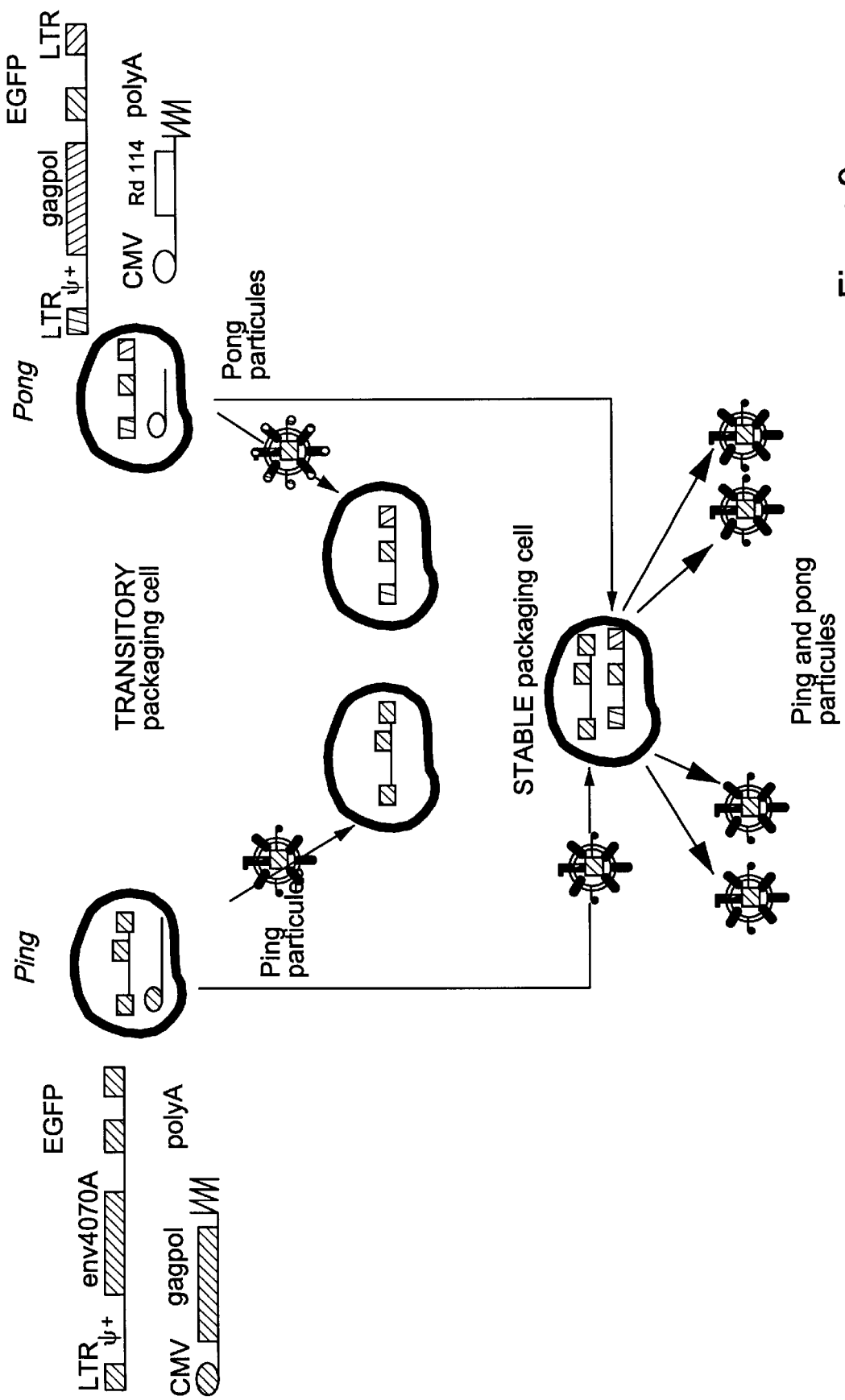

In a particular embodiment, they are used essentially simultaneously. For instance, a cell, culture, tissue, organ or the like is contacted with each of the retroviral constructs, essentially at the same time. For this purpose, the retroviral constructs can be contained in the same composition, which is added to the cell, culture, tissue, organ or the like, or in separate medium/compositions/devices, which are added essentially simultaneously to the cell, culture, tissue, organ or the like. Essentially simultaneously indicates that there is no requirement for precise timing of the addition and that time differences are tolerated and do not affect the transduction efficiency of the instant invention. Once the retroviral constructs have been contacted with the cells, they penetrate into the cells and the retroviral genomes integrate into the transduced cells' genome. In cells which contain the two constructs, trans-complementation leads to replication and packaging of both viral genomes. The viruses released from these cells are, again, semi-replicating, i.e., upon co-infection of a cell, they will transcomplement each other to produce further viruses and transduce further cells. According to this system, which is illustrated in FIG. 9, the polynucleotides are delivered efficiently and spread in surrounding cells, tissues or organs.

Figure 10:
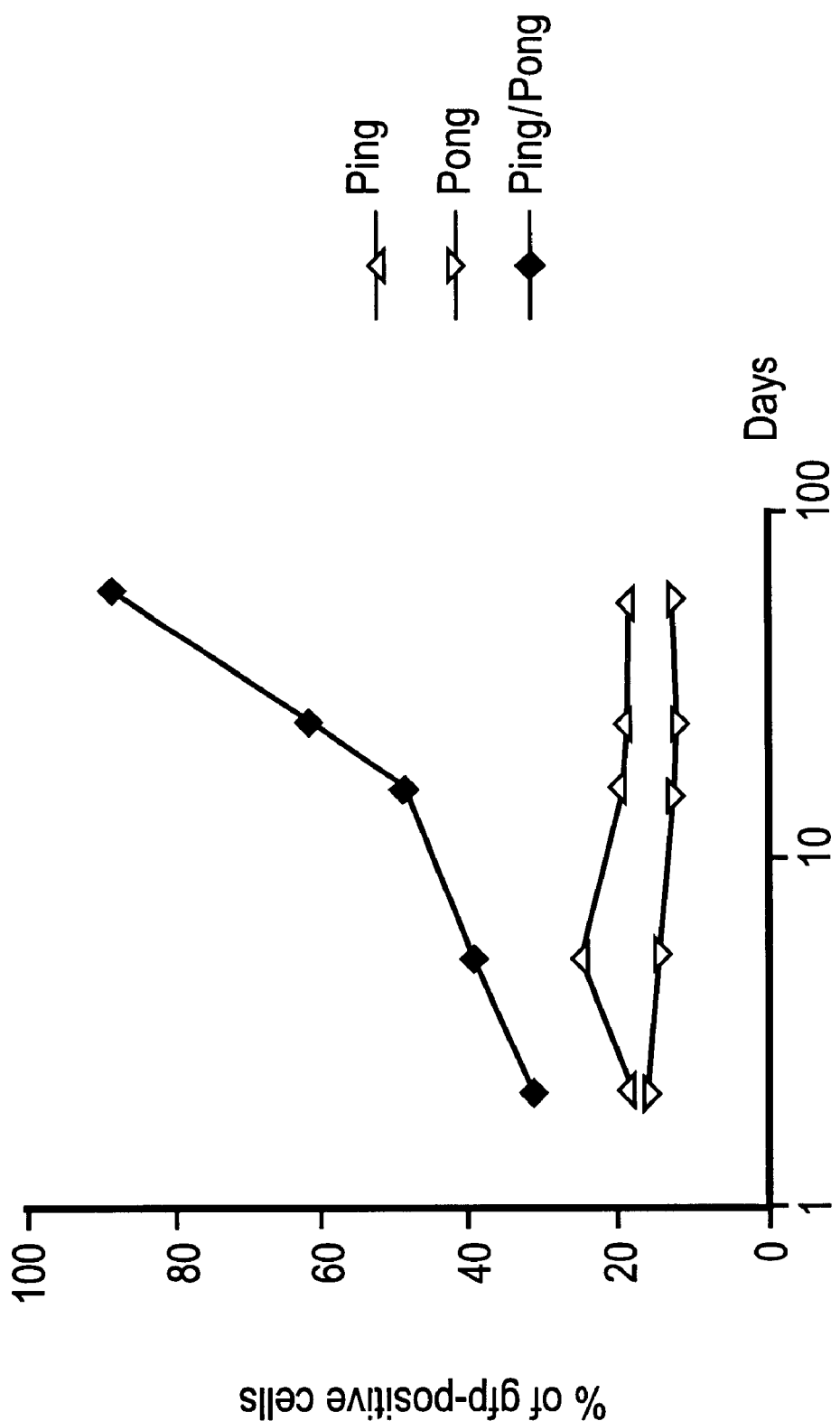

In another embodiment, the semi-replicating viral constructs are used sequentially, i.e., at different point in time. For instance, a cell, culture, tissue, organ or the like is first contacted with one of the semi-replicating retroviral constructs. The retroviral construct penetrates into the cells and the retroviral genome integrates into the transduced cells' genome. Such a cell thus produces either env-devoided viral capsids (with a gp retroviral genome, for instance), or envelop proteins (with the second or third retroviral genome, for instance). The cells also contain and express the polynucleotide delivered by the recombinant genome. If the transduction efficiency with the first viral construct is deemed to be insufficient to obtain appropriate or optimal biological effect, the cells, culture, tissue, organ or the like can then be contacted with a second (or more) semi-replicating constructs which transcomplement the first one. As in the preceding scenario the cells which contain the two constructs replicate and lead to packaging of both all types of viral genomes. The viruses released from these cells are, again, semi-replicating, i.e., upon co-infection of a cell, they will transcomplement each other to produce further viruses and transduce further cells. According to this system, which is illustrated in FIGS. 9 and 10, the polynucleotides are delivered efficiently and spread in surrounding cells, tissues or organs.

Accordingly, any combination of semi-replicating viral constructs can be used, essentially simultaneously or sequentially, to deliver polynucleotides to a cell, culture, tissue, organ, or the like, in vitro, ex vivo or in vivo. The system is very efficient since, as illustrated in the examples and figures, more than 85% and up to about 100% of a HCT116 cell culture effectively contain the polynucleotide upon contacting with retroviral constructs of the instant invention.

The Polynucleotide

The instant invention can be used to deliver essentially any polynucleotide to a cell, culture, tissue, organ or organism. More preferably, the polynucleotide may be any DNA, cDNA, synthetic or semi-synthetic DNA, RNA, mRNA, etc. The polynucleotide preferably comprises less than 10 kb, more preferably less than 5 kb. Preferred polynucleotides to be used in the instant invention comprise between 200 and 4000 bp. The polynucleotide may additionally comprise a promoter region or other expression signals although, as explained above, the presence of such elements might not be necessary to ensure proper expression.

Preferably, the polynucleotide is heterologous with respect to the retroviral construct, i.e., does not originate from the retrovirus used in the production of the constructs. However, as indicated before, the polynucleotide may also encode viral or retroviral proteins, such as for instance fusogenic retroviral envelope proteins (VSV-G, GALV, etc.) or immunogenic envelope proteins, such as HIV envelope, polio envelope, or modified envelope proteins comprising an antigenic peptide in their sequence. In such embodiments, the polynucleotide would substitute for the env or corresponding retroviral gene. Particular examples include MOMLV retroviral constructs pseudotyped with a heterologous envelope protein-encoding nucleic acid, e.g., a HIV envelope. In such an embodiment, the polynucleotide is the env gene.

Alternatively, the env gene may be modified to contain a sequence encoding an antigenic peptide. In this embodiment, the polynucleotide is therefore a nucleic acid encoding the retroviral, modified, envelope protein.

In another embodiment, the retroviral construct is of the MoMLV type, the envelope is of a different type (e.g., HIV), and the polynucleotide encodes an immuno-stimulating polypeptide, such as a cytokine (e.g., IL-2).

The polynucleotide may encode any product of interest, including one or several RNA, peptide, polypeptide and/or protein. The product encoded may exhibit biological activity, such as therapeutic or immunogenic activities. It may also exhibit toxic activity, a marker property, antisense activity, etc. It is believed that the instant invention can be used by the skilled artisan with essentially any kind of polynucleotide.

The polynucleotide preferably encodes a product which is biologically active in mammalian cells such as human cells.

Examples of polynucleotides include any suicide or toxic gene, in particular conditionally toxic genes such as thymidine kinase, cytosine desaminase, or the like, or other bacterial toxins or fusogenic retroviral envelopes. The polynucleotide may also encode tumor suppressor proteins, such as p53, Rb, E1, BRCA1, etc., cytokines (e.g., IL-2, or any other lymphokines such as TNF, IFN, etc.), antiangiogenic factors, antigenic peptides, growth factors (G-CSF, GM-CSF, BDNF, CNTF, etc.) and the like. The polynucleotide may also encode single chain antibodies, antisense RNAs, Ribozyme and the like.

Control of the Virus Spread

As mentioned before, the invention stems from a new concept of using replication-competent viral constructs to deliver genes to cells, in vitro or in vivo. In the prior art, efforts have always been made in order to avoid replication of recombinant viruses (complex packaging cells, highly deleted viral constructs, etc.). The invention now claims that replication of viral constructs can be tolerated, and takes advantage of said replication to increase polynucleotide delivery and expression. It is indeed proposed that replication of some retroviruses (such as MOMLV retroviruses) would not induce significant pathological condition in subjects. In particular, it is proposed that such potential adverse effects (i) are strongly balanced by the biological benefits obtained by this delivery system and (ii) can be controlled by several methods and constructs (for instance where other retroviruses are being used). For this purpose, several strategies are possible, which represent preferred, specific embodiments of the instant invention. These strategies can be used alone or in combinations.

As a preliminary remark, it should be noted that certain retroviruses, such as MoMLV essentially infect dividing cells, so that the spread of the retroviral genomes constructed with MOMLV sequences is limited to such dividing cells and would not normally extend to quiescent cells. However, even where other retroviruses are used, such as lentiviruses, which infect also quiescent cells, virus spread may be controlled or limited using any one of the following methods or constructs, either alone or in combination(s).

In one particular embodiment, the virus spread is further controlled by retargeting the viruses. Indeed, the tropism of a retrovirus is determined essentially by the envelope glycoprotein. The retroviral surface protein SU of the envelope is mainly responsible for the binding of the virus to a specific cell surface receptor, and the TM subunit triggers post-binding events, leading to membrane fusion and viral entry (Ragheb et al., J. Virol. 68 (1994) 3207). It has been disclosed that the envelope glycoprotein can be modified, for instance to incorporate specific receptor ligand or receptor fragment, and that the resulting envelope proteins provide targeted infection of cells expressing said receptor or ligand. Accordingly, in order to control spread of the viruses, in a preferred embodiment of the invention, the envelope protein encoded by the replicating or semi-replicating viral genomes has a modified tropism that retargets the specificity of retroviral attachment. Examples of such envelope proteins with modified tropism include membrane proteins with affinity for CD4, retroviral envelope proteins comprising a TM subunit fused to a peptide, such as a Hepatocyte Growth Factor fragment (Nguyen et al., Hum. Gene Ther. 9 (1998) 2469), as well as amphotropic envelope proteins fused, at their N-terminal end, with ligands such as single chain antibodies, for instance.

Virus spread can also be controlled by the use of tissue specific and/or regulated (e.g., inducible) promoters, i.e., promoter regions which are particularly active in preferred cells, tissues or organs and/or under certain conditions. In this regard, targeted expression control can be introduced at various levels, depending on the structure of the viral constructs which are being used. For instance, where the polynucleotide comprises its own promoter region, targeted expression of the polynucleotide can be accomplished by introducing a selective and/or regulated promoter in said polynucleotide. Alternatively, where expression of the polynucleotide is controlled by the promoter region of the LTR, it is possible to modify the LTR region in order to confer selective and/or regulated expression thereto. In this respect, the 3' U3 region of the LTR can be engineered with any tissue selective/regulated regulatory sequence, so that, after reverse transcription, the 5' LTR controls viral genes and polynucleotide expression with said regulatory sequences.

Several candidate selective and/or regulated promoter or regulatory regions can be used, such as promoter (or fragments thereof) allowing preferential and/or regulated expression in certain tumor cells (e.g., hepatocarcinoma, colon carcinoma, glioblastoma) or other abnormally proliferating cells, including for instance cells of the hematopoietic or nervous system. Particular examples of selective and/or regulated promoters include for instance:

- the alfa-fetoprotein (AFP) promoter, which is expressed in about 40% of primary liver tumors (Mawatari et al., Cancer Gene Ther. 5 (1998) 301). Previous studies have shown that human AFP promoter allows preferential expression of a reporter gene in hepatocarcinoma cells. Furthermore, selective hepatocarcinoma expression with AFP promoter has been observed in the context of retroviral vectors.
- the Aldolase A promoter, which is expressed in liver tumors, particularly in patients with HCC (Moch et al., Transgenic Research 7 (1998) 113; Guillouzo et al., J. Cell Sci. 49 (1981) 249).
- the Pancreatic-associated protein (PAP/HIP) promoter, which is overexpressed in up to 70% of hepatocarcinoma (Christa et al., J. Hepatol. 30 (1999) 105). The PAP/HIP promoter appears to be tightly regulated in HCC cells, and a 1.3 kb fragment thereof directs highly preferential expression into HCC cells.
- the carcinoembryonic antigen (CEA) promoter, which is particularly active in colon carcinoma (CC). This promoter has already been shown to remain selective in a viral context (Richards et al., Hum. Gen. Ther. 6 (1995) 881).
- the glial fibrillary acidic protein (GFAP) promoter and the myelin basic protein (MBP) promoter, which have both been shown to preferentially initiate transcription in glioblastoma cells (McKie et al., Gene Ther. 5 (1998) 440; Morelli et al., J. Gen. Virol. 80 (1999) 571).
- interleukin promoters, which may be used to provide preferential expression in certain hematopoietic cells,
- any promoter, including tissue-selective promoters (such as neural and endocrine promoters with neuronal, glial and pituitary specific activity for instance) combined with regulatory sequences, such as the tetracycline-regulatable expression sequences (Smith-Arica et al., Cold Spring Harbor, Spring Meeting, 1999) or any other modified transcriptional activator.

It should be understood that any other promoter or regulatory sequence conferring selective and/or regulated expression may be used by the skilled artisan.

In another particular embodiment, the virus spread is controlled by the product encoded by the polynucleotide itself. For instance, the polynucleotide may comprise a sequence encoding a (conditionally) toxic molecule, that can be used to destroy infected cells. Such a conditionally toxic molecule can be for instance a thymidine kinase, cytosine desaminase, derivatives thereof and the like, which are able to convert a metabolite (e.g., a nucleoside analog or 5-FU, respectively) into a product which destroys the infected cells. The sequence encoding a (conditionally) toxic molecule may be added into the polynucleotide, in combination with another coding sequence producing a biological product. It may of course be used also as a biologically active gene/product, for instance for cancer treatment. The polynucleotide may also encode other toxic molecules such as fusogenic envelope proteins, leading to infected cell death.

In another particular embodiment, the replicating or semi-replicating viral construct encodes a polypeptide that renders infected cells sensitive to immune cells and thus causes or stimulates their elimination by the host organism. A particular example of such a polypeptide is a-galactosyl transferase (αGAL4), as described in Gollogly et al (Neoplasma 43 (1996) 285). αGAL4 is a bacterial enzyme not expressed in human cells, which creates particular glycosylation is motifs. More particularly, αGAL4 introduces alpha(1–3) galactosyl motif on glycolipids, which motif is not present on human cells. This motif is however expressed by many bacteriae, and human beings have high levels of natural antibodies directed against it. By introducing a nucleic acid encoding such a polypeptide in the replicating or semi-replicating viruses of the present invention, the viral particles can be neutralized and infected cells destroyed by the host's immune system, thereby controlling viral spread. Furthermore, the αGAL4 may also act as the therapeutic gene or product, where destruction of diseased cells (such as tumor cells) is sought. In this regard, in a particular embodiment, the present invention resides in a replicating or semi-replicating viral constructs comprising a nucleic acid encoding a αGAL4 polypeptide.

Other examples of such polypeptides include antigenic peptides, more preferably from microorganism against which people are or can be vaccinated (such as antigenic peptide from tetanus toxoid or from hepatitis) and/or immuno-stimulating molecules (such as interleukin-2 for instance or other cytokines). Expression of such polynucleotide raises an immune response of the host against said peptides, proteins and/or molecules, leading to an immune reaction against cells infected with the retroviral constructs. This immune response therefore (i) produces the expected biological effect of polynucleotide delivery and expression and (ii) leads to an elimination of infected cells in the organism. Accordingly, the use of the instant invention to raise an immune response (i.e., cellular or antibody) is advantageous since it has the effect of controlling virus spread when the desired immune effect is obtained.

In this regard, a particular embodiment of this invention resides in a composition of replicating or semi-replicating viral constructs as defined above, wherein said viral constructs comprise, in combination or separately, a polynucleotide encoding αGAL4 or an antigenic peptide and a polynucleotide encoding a cytokine, more preferably IL-2. More preferably, the composition comprises at least a first replicating or semi-replicating viral construct comprising a polynucleotide encoding αGAL4 or an antigenic peptide, and at least a second replicating or semi-replicating viral construct comprising a polynucleotide encoding a cytokine, more preferably IL-2, for simultaneous, separate or sequential use.

Still another approach to control virus spread in vivo, comprises the administration of neutralizing compounds, such as neutralizing antibodies or antiviral compounds, which can inactivate the retroviruses. In this regard, several retrovirus-neutralizing monoclonal antibodies have been disclosed in the prior art. When the vector comprise an antigenic peptide from a micro organism such as tetanus toxoid, immune sera raised against this microorganism that are commonly used in the clinic can be used advantageously in this setting. Suitable anti-viral compounds also include, for instance, AZT (zidovudine) or other didesoxynucleotide analogs such as DDC (didesoxycytosine) and DDI (didesoxyionisine), antiproteases, such as protease p12 and protease p15 inhibitors, combinations thereof, vaccines and the like. In a particular embodiment, the method of delivering polynucleotides in vivo of the present invention therefore comprises the co-administration of (i) replicating or semi-replicating retroviral constructs as disclosed above and (ii) a neutralizing compound, such as a neutralizing monoclonal antibody (or derivatives thereof such as Fab fragments, single chain antibodies, etc.) or an anti-viral compound or treatment. In a particular embodiment, the replicating or semi-replicating retroviral constructs are administered in a tissue or organ and the neutralizing compound is administered by intravenous injection, for instance. Co-administration does not imply simultaneous administration, but indicates that, in order to provide control over virus spread, the neutralizing molecules should be administered (i.e., either prior to the retroviral constructs, or at about the same time, or even subsequently).

Moreover, control of virus spread may also be achieved advantageously by using retroviral constructs with (modified) envelope proteins against which the host organism is already immunized, or can be easily immunized. In this regard, where the host already exhibits anti-env antibodies, viral spread will be limited. Alternatively, in order to control virus spread, the host subject may be immunized, prior to or at about the same time, or after administration of the retroviral construct (e.g., by using a polio vaccine where the retroviral construct is pseudotyped (expresses) the polio envelope, optionally in combination with other retroviral envelopes, such as MOMLV or HIV envelopes). Alternatively, the envelope protein may be modified as described above, to contain an epitope that is recognized by antibodies or immune cells of the host organism. In this regard, epitopes may be introduced in the envelope protein without significantly altering the activity of the envelope, said epitopes being exposed at the surface of the viral particle or at the surface of cells infected therewith. The epitope may be selected among epitopes against which human beings are or can be easily immunized. Such epitopes include for instance any immunogenic peptide derived from tetanus toxin, flu virus, poliovirus, measle virus, hepatitis viruses . . . The epitope or peptide, should be of sufficient size to ensure a proper conformation allowing recognition by antibodies or could be short sequences generally below 20 amino acids, more preferably below 15 amino acids, when recognition by CTLs is sought. The antigenic peptide is preferably introduced at the C-terminal end of the envelope, to ensure exposure thereof. Upon administration (or in vivo production) of such viruses, the viral particles that disseminate can be neutralized and eliminated by antibodies of the host and the infected cells destroyed by antibodies or immune cells. In this respect, in a particular embodiment, the epitope(s) comprises at least a class I CMH epitope, that is recognized by CTL lymphocytes, leading to elimination of infected cells. These represent particular embodiments and methods/or controlling viral spread.

Envelope Modification to Increase Packaging Efficiency

As mentioned above, the inventors of the present invention have surprisingly shown that the env gene exerts a negative effect on encapsidation of a retroviral genome in a retroviral particle. This unexpected discovery opens new strategies to increase retroviral vectors' packaging efficiency by modifying the env gene. In this regard, the invention also resides in a method of increasing packaging efficiency of a retroviral vector, the method comprising modifying the env gene in said retroviral vector to create a non-functional env gene. Modification more preferably comprises deleting all or part of the env gene, more preferably the entire env coding sequences. This method can be applied to all types of retroviral vectors as mentioned above, and is particularly suited for producing inter-dependent retroviral vector systems in which at least two retroviral constructs are being used (either simultaneously or sequentially), one of which being env-defective.

As will be disclosed in the following examples, the instant invention now provides very efficient compositions and methods for delivering polynucleotides to cells in vitro, in vivo or ex vivo. The invention can be used for experimental research, clinical research, in human and/or animal, as well as for therapeutic, diagnostic or prophylactic treatments.

LEGEND TO THE FIGURES

FIG. 1: Construction of plasmid pGH45

Figure 2:
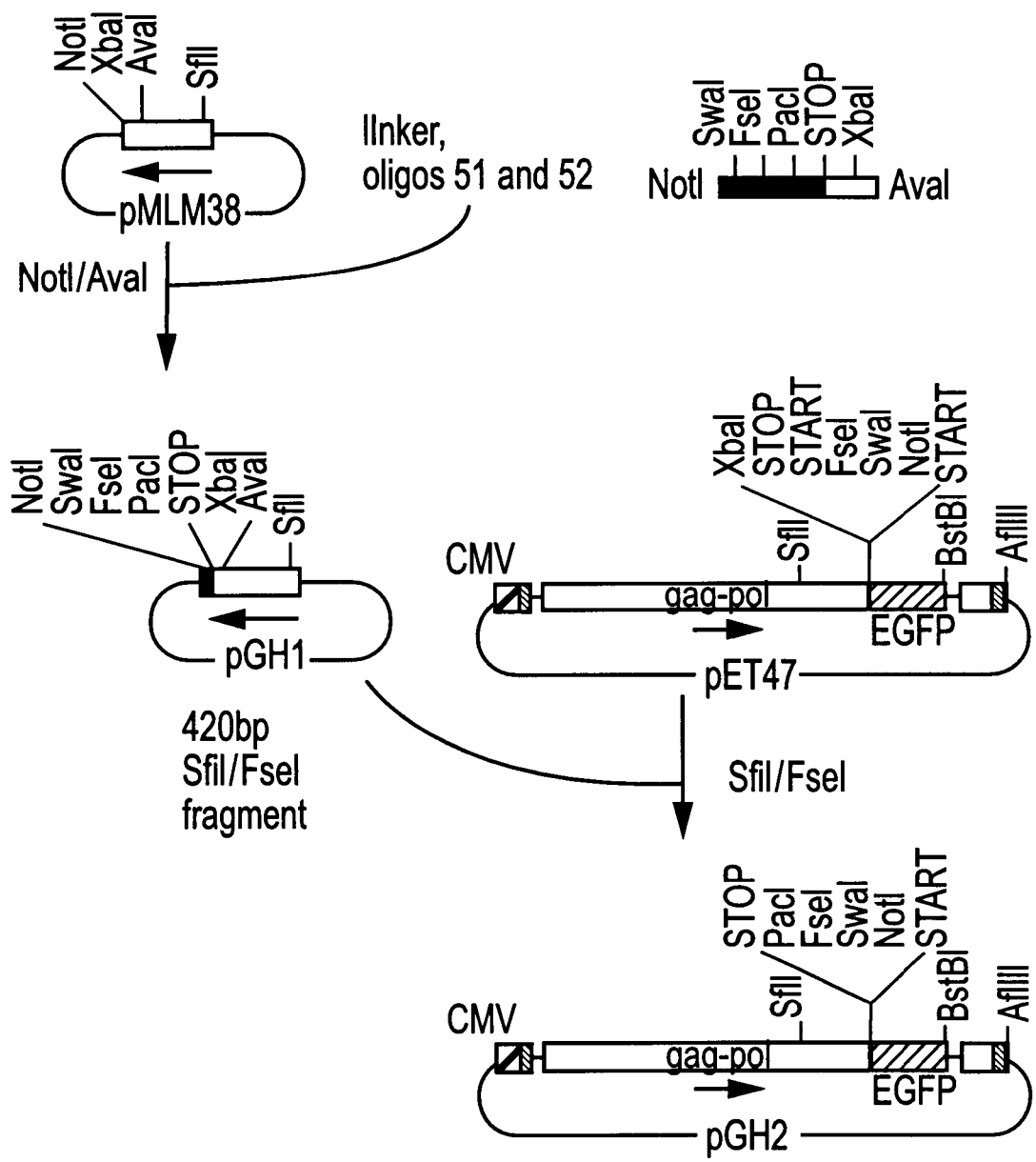

FIG. 2: Construction of plasmid pGH2

Figure 3:
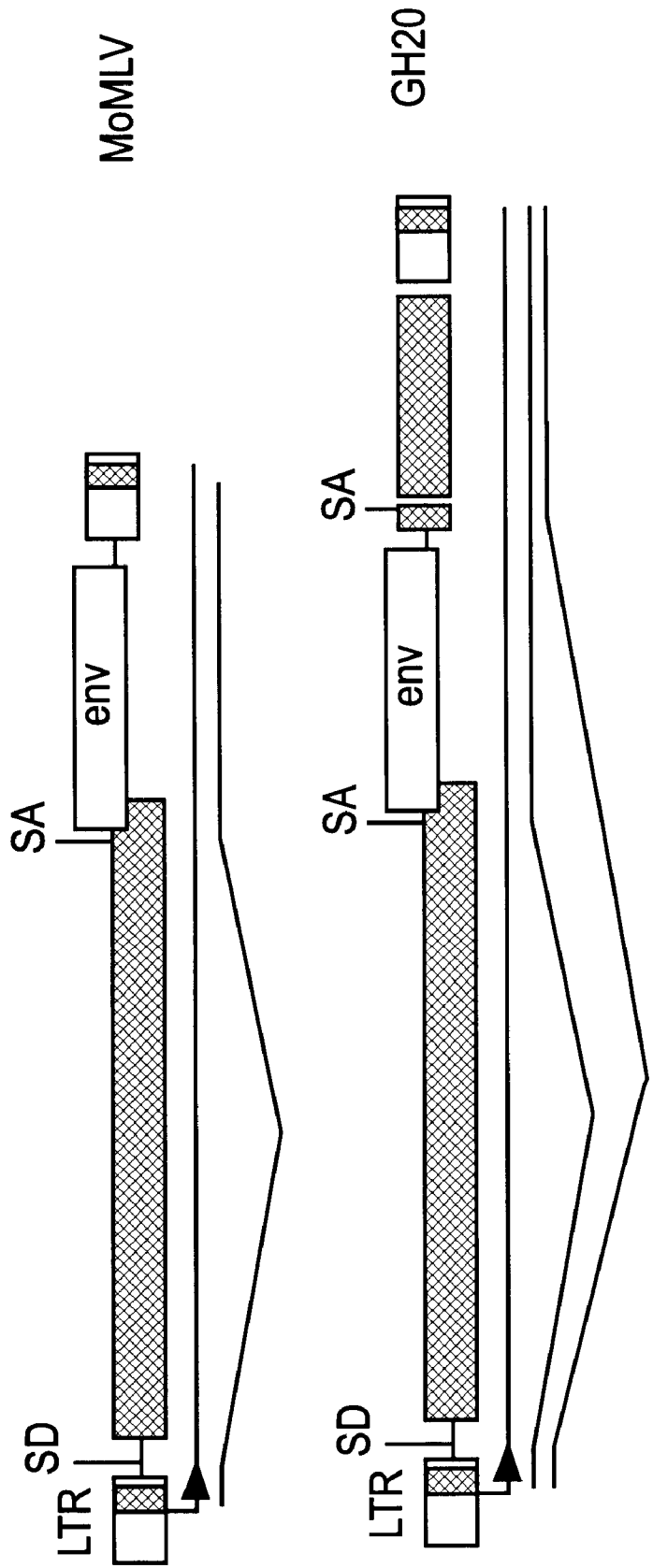

FIG. 3: Molecular design of the replication competent MOMLV vector. In MOMLV, the open reading frames gag-pol and env are expressed from a common promoter in the 5'-LTR (arrow) by alternative splicing. To construct the replication competent vector GH20, an additional splice acceptor site was introduced downstream of the env gene of MoMLV by duplicating 0,4 kb of the pol sequence containing the natural acceptor region (SA). The reporter gene EGFP was placed downstream of the second SA. The spacing between the SA site and the start codon of the transgene is similar to that of the env transcription unit.

FIG. 4: Propagation of the vector. Subconfluent monolayers of NIH 3T3 cells were infected with the replicative construct GH20 (A) or with a non replicating EGFP expressing vector (B) at a low m.o.i. Fluorescent focuses were photographed 3 days post infection.

Figure 5:
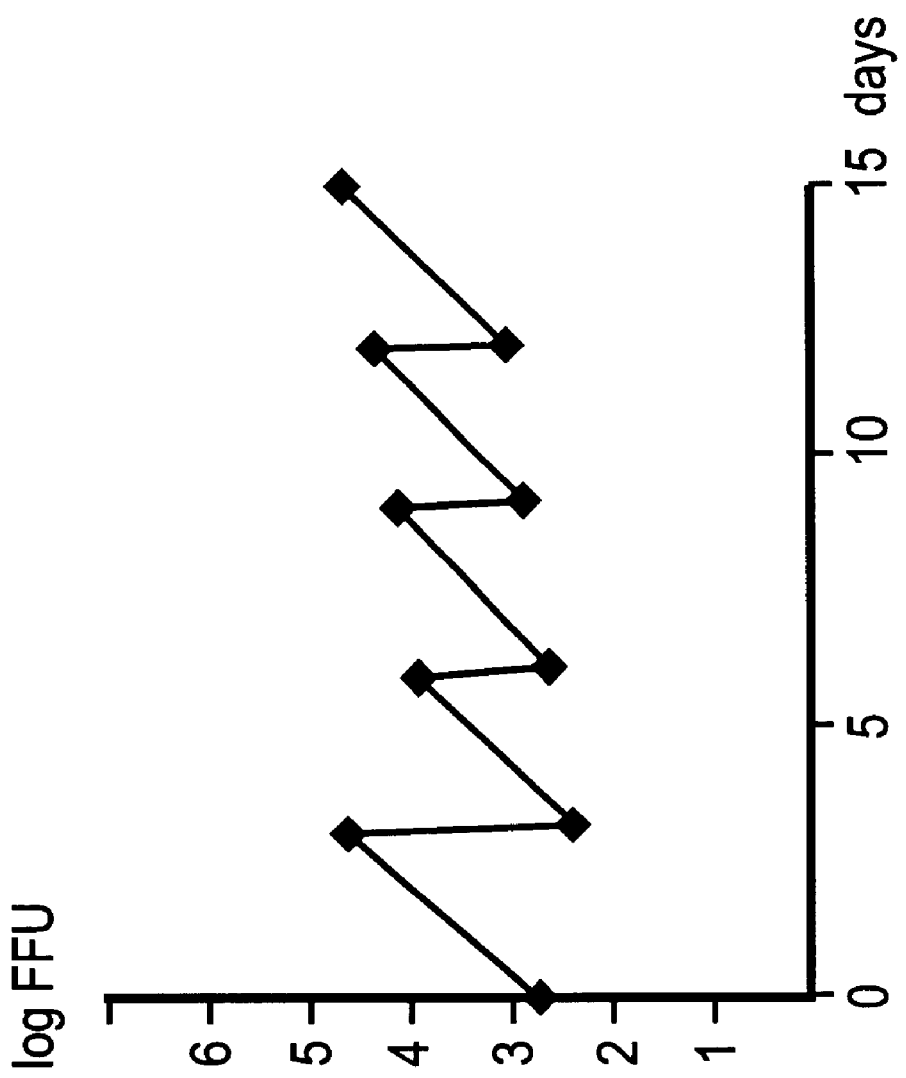

FIG. 5: Serial infections. NIH 3T3 cells were infected with the vector GH20 at maximal $10^3$ focus forming units per well. After 3 days supernatants were harvested and diluted for the next round of infection. The supernatants were tittered on NIH 3T3 cells by fluorescence microscopy.

Figure 6A:
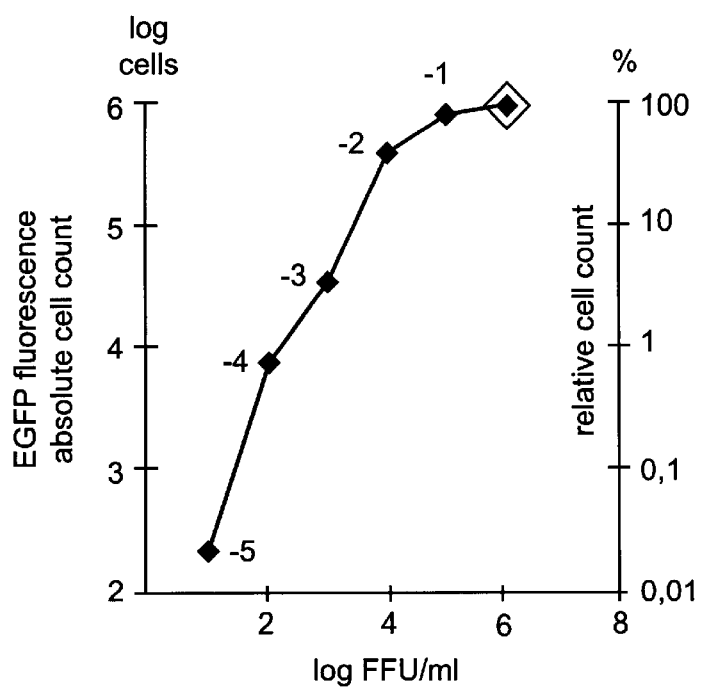
Figure 6B:
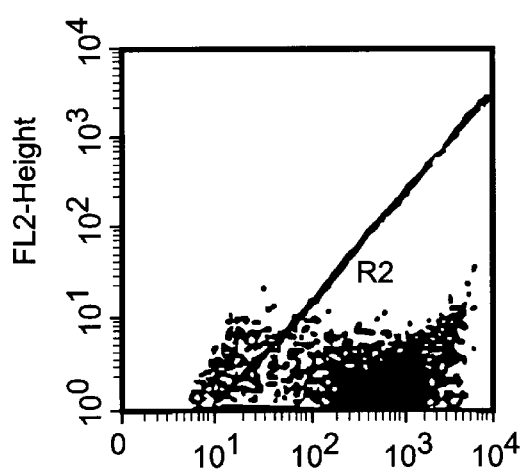
Figure 6C:
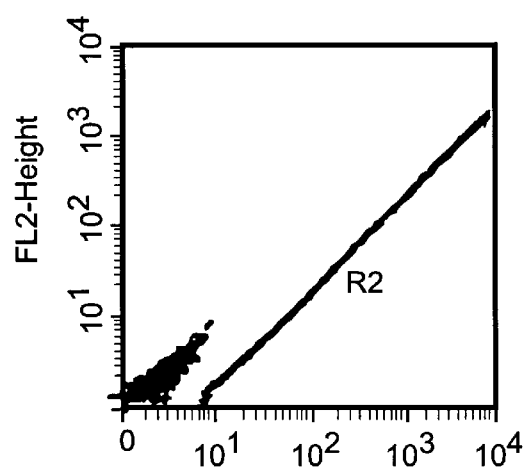

FIG. 6: Titration of the vector. 500 $\mu$l of supernatant from a GH20 producer cell pool was used to infect $10^5$ NIH 3T3 cells. Three days post infection, the titer was estimated by fluorescence microscopy. The titer was compared to the percentage of EGFP expressing cells as determined by FACS (A). In order to disclose the settings for the FACS analysis, the infection with undiluted supernatant (B) and uninfected NIH 3T3 cells (C) are shown.

FIG. 7: PCR assessment of wt rearrangements.

A) A vector specific PCR product was amplified spanning from the MOMLV env to the 5'-terminus of the EGFP reporter gene.

B) A primer pair binding to the env gene and to the U3 region of the LTR, respectively, gives a 1 kb fragment with MoMLV wt DNA as template. A vector specific fragment of the theoretic size of 2 kb is not amplified under the chosen parameters. Lysates of $5\times10^4$ cells per reaction were analyzed, control reactions (lanes 1–3) were performed in an equivalent background of NIH 3T3 genomic DNA.

Figure 8:
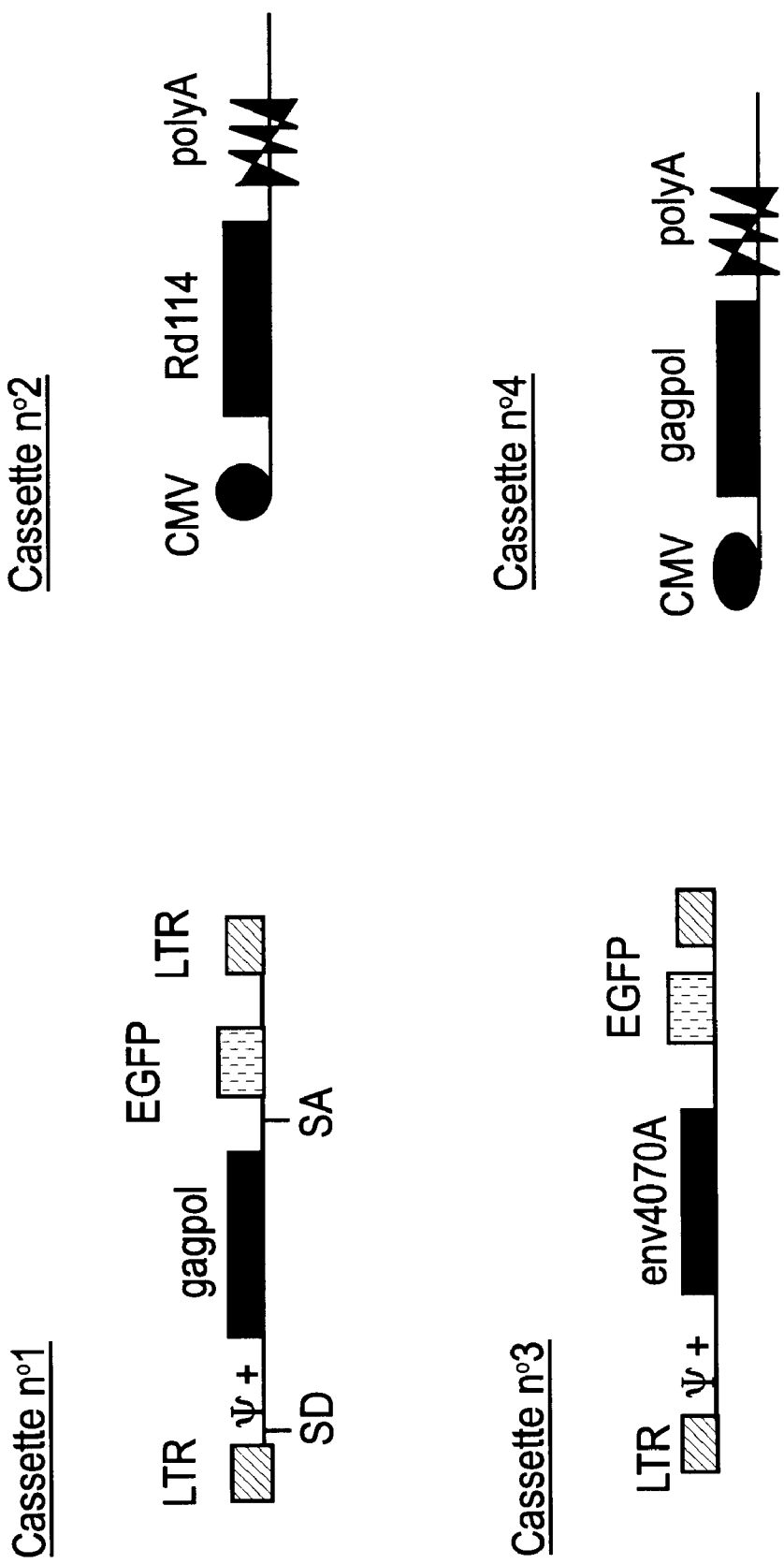

FIG. 8: Structure of the different expression cassette (SD=Splice Donor site; SA=Splice Acceptor site; CMV= Cytomegalovirus enhancer and promoter sequences; LTR= Long Terminal Repeat; ψ=encapsidation recognition signal; polyA=SV40 polyadenylation signal).

FIG. 9: Concept of YING-YANG retroviral plasmids. Ying or Yang transfected cells produce ying or yang particles, respectively, in a transitory manner. Cells doubly infected with ping and pong particles stably produce new retroviral particles.

FIG. 10: Proof of the concept of the ying-yang effect. HCT116 colonic carcinoma cells were transfected by either ping or pong plasmovirus alone (at day 0), or successively by ping (at day −15) and pong plasmoviruses (at day 0). The expression of the EGFP transgene is observed following these transfections. There is a clearly synergistic effect of these plasmids. This experiment has been reproduced five times: the same results are obtained in 293 human cell line, or in HCT116 when the pong plasmovirus is transfected before the ping plasmovirus.

FIG. 11: Sequence SEQ ID NO:6. Nucleotide position 1 corresponds to nucleotide 7801 in pGH45. Element (I) at nt 427 is the stop codon of env. Element (II) at nt 437 represents the beginning of repeated pol region containing the SA site, which ends at element (IV), at nt 802. This region 437–802 is a particular fragment comprising a splice acceptor site. Element (III), nt 532–nt 540 represent the splice acceptor site. Element (V) at nt 840 (ATG) is the start codon of EGFP gene.

Figure 12:
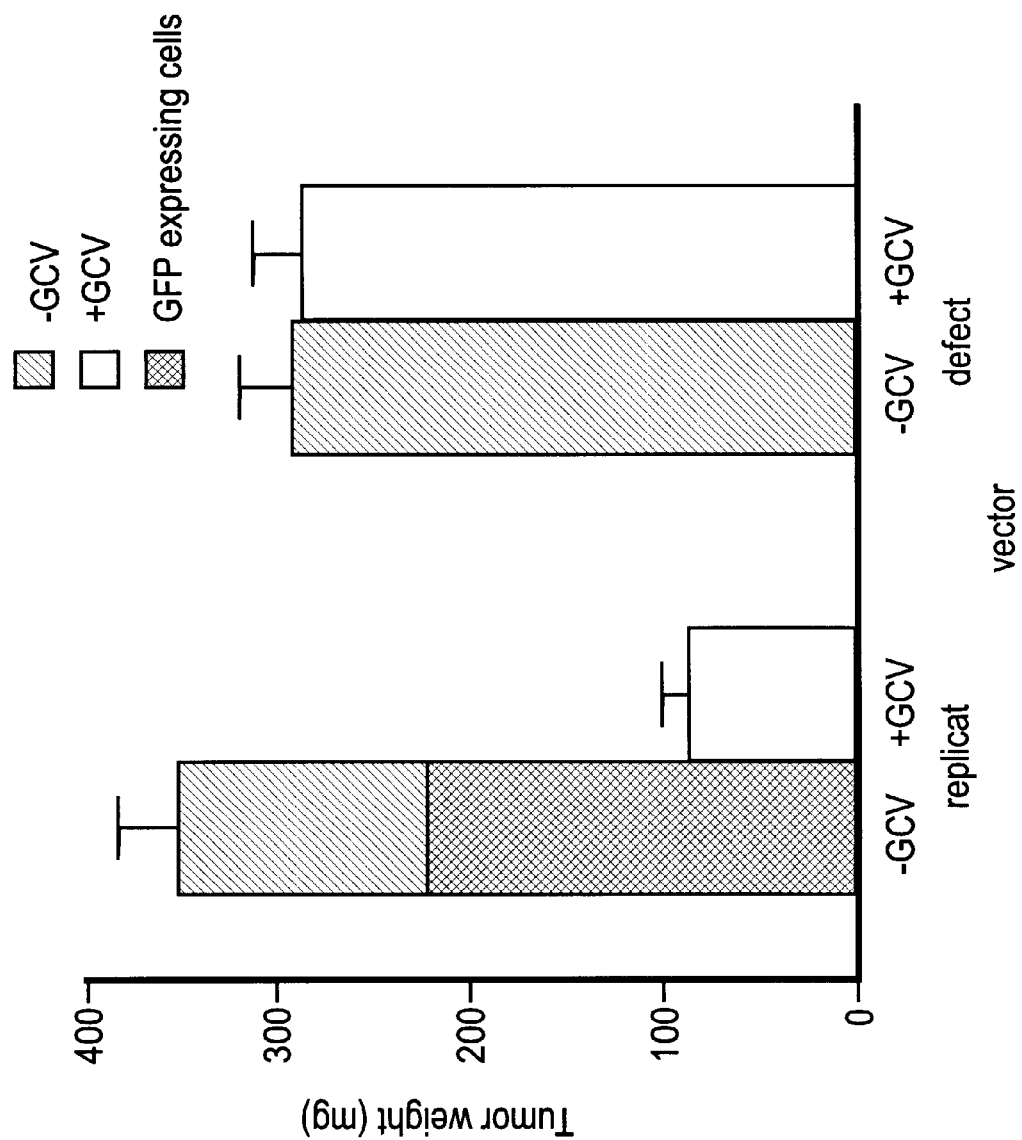

FIG. 12: Comparison of transgene expression and therapeutic gene transfer efficacy using replicative or defective retroviral vectors transducing a TK/GFP fusion protein. Bars represents the mean tumor weight for tumors transduced with a replicative or defective vector, and treated or not with ganciclovir. For each group, the proportion of GFP expressing cells is indicated by the dashed area of the bar.

Figure 13:
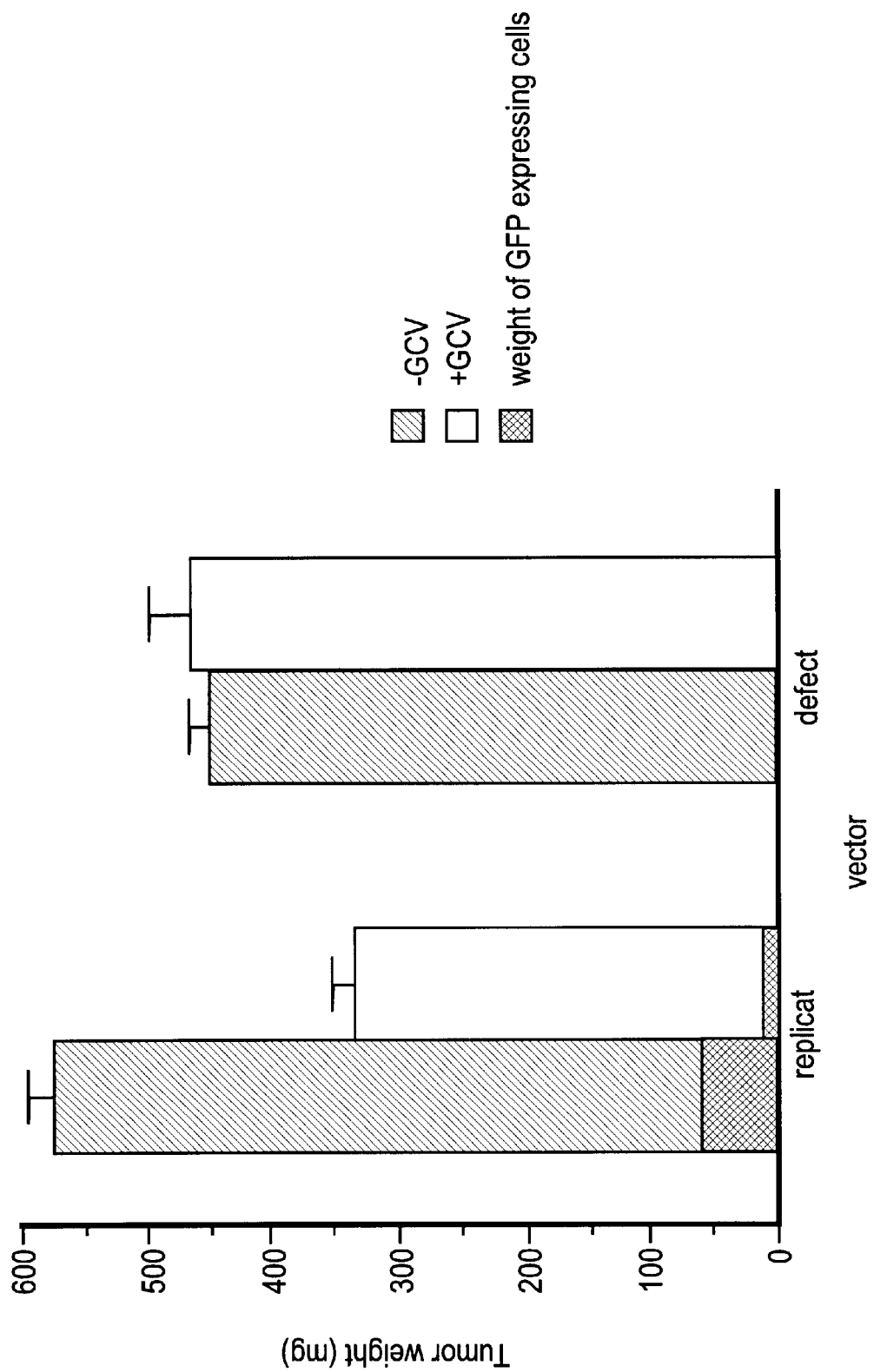

FIG. 13: Treatment of established tumor by replicative or defective vectors transducing a TK/GFP fusion gene.

EXAMPLES

A-Preparation and Uses of Replicating Viral Constructs

In order to construct the replicating MOMLV vector pGH45, the reporter gene was placed downstream of the env gene, preceded by a copy of the viral splice acceptor region. The constructs described are of the genomic structure LTR-gagpol-env-EGFP-LTR. Between the env gene and the EGFP reporter gene a 0,4 kb fragment of the MoMLV pol gene, containing the known critical regions of the splice acceptor, were inserted. The mechanisms of splice control in MoMLV are not well understood so far. While expression levels of the transgene depend on the acceptance of the additional splice acceptor, over-splicing at this site is expected to abolish virus growth by reduction of the amount of full length genomic RNA, or by interference with the processing of the env message. Surprisingly, the chosen configuration allows both efficient expression of the reporter gene and replication of the viral vector.

Furthermore, the intended attenuation of the vector by targeted deletion of the env gene in GH45 was observed at high frequency. Clones of infected cells were tested for the expected deletion by PCR (data not shown). About 30% (8 from 28) of the EGFP expressing clones, isolated after three rounds of infection, displayed the env deleted structure in PCR testing.

A.1. Construction of the Replicative Vector pGH45 (FIGS. 1–3)

The plasmids pMLM38 et pET47 were used as a source for the sequences around the splice acceptor site to be introduced into the vector. The transcriptional start site of the transgene at the intended splice acceptor site contained an additional aberrant ATG signal and was corrected as follows:

pGH1

The plasmid pMLM38 was cut with Notl and Aval and a synthetic linker consisting of the oligonucleotides GH51 (5'-GGCCGCTA TTTAAATGGC CGGCCTTAAT TAAAGTCTAG AGGATGGTCC ACCC; SEQ ID NO: 2) and GH52 (5'-CCGGGGGTG GACCATCCTC TAGACTT-TAA TTAAGGCCGG CCATTTAAAT AGC; SEQ ID NO: 3) was inserted. The resulting plasmid was termed pGH1.

pGH2 (FIG. 2)

A 0,4 kb fragment containing the corrected region was isolated from pGH1 by Sfil and Fsel digestion and cloned into Sfil/Fsel cut pET47. The resulting plasmid pGH2 is identical to pET47 with exception of the improved transcriptional start region of the transgene.

The assembly of the replicative vector pGH2, containing the entire MoMLV proviral genome, including the open reading frames gap-pol and env and the EGFP reporter gene was done as follows:

pGH10

The 3' prime portion of the MOMLV env gene was amplified as a 0,75 kb PCR fragment with the primers GH10 forward (AGTACCGGGA TTAATCCATG CATCTCCACC ACCATACTG; SEQ ID NO: 4) and GH10 reverse (TATGGTCTCT AGACATATGC TAT GGCTCGT ACTC-TATAGG CTTCAGC; SEQ ID NO: 5) and the plasmid pNca as template. The PCR product was cut with the enzymes Asel and Xbal and ligated int Ndel/Xbal cut pUC 18 to give pGH10.

pGH11

The plasmid pGH2 was digested with Ndel and Sacl to isolate a 1,6 kb fragment containing 400bp of the 3'-terminal of the MoMLV pol gene, the entire EGFP reading frame and 3'-LTR sequences. Ligating this fragment to Ndel/Sacl cut pGH 10 resulted in the plasmid pGH 11.

pGH12 pGH11 was cleaved with Nhel and Aflll to insert a 0,75 kb fragment from pNca (Colicelli J., J. Mol. Biol. 199 (1988) 47–59) thereby completing the 3'-LTR. The resulting plasmid was termed pGH12.

PGH20

A bp fragment was obtained by digestion of pGH12 by the enzymes Nsil and Aflll. This fragment was ligated into Nsil/Aflll cut pNca to give pGH20. The plasmid pGH20 contains a functional replicating EGFP expressing retroviral genome.

The elements of the vector pGH20 are mapped as follows (see FIGS. 1 and 3):

1–593 5'-LTR
1070–2684 gag, complete coding sequence
1070–6284 gag-pol, complete coding sequence
5942–5951 splice acceptor site
6226–8223 env ecotropic, complete coding sequence
8231–8596 pol sequences, partial (Ndel-Xbal)
8316–8325 splice acceptor site (SEQ ID NO: 6)
8634–9353 EGFP gene, complete coding sequence
9416–10008 3'-LTR The vector pGH20 was improved by deleting plasmid sequences that lead to homologous recombination and thus to occasional wt-formation during replication. The improved construct designated pGH45 was constructed as follows (see FIG. 1):

pGH43

In order to manipulate the region upstream of the 5'-LTR, the 3'-half of the retroviral sequences were deleted from the plasmid pNca by digestion with the enzymes Ncol and Aflll and religation. The resulting plasmid was termed pGH43.

pGH44 pGH43 was cleaved with EcoRI and NheI and a synthetic linker consisting in the annealed oligonucleotides GH43/1 AATTCAATGA AAGACCCCAC CTGTAGGTTT GGCAAC ; SEQ ID NO: 7) and GH43/2 (CTAGGTTGCC AAACCTACAG GTGGGGTCTT TCATTG; SEQ ID NO: 8) was inserted. Thus, in the resulting plasmid pGH44, 160bp of the plasmid sequence upstream of the proviral genome are removed.

pGH45

A 4,2 kb fragment containing the corrected sequence was isolated from pGH44 by EcoRI/SalI digestion and ligated into EcoRI/SalI cut vector pGH20. The resulting corrected plasmid is termed pGH45 and is of the same proviral sequence as pGH20.

Structural map of pGH45

7–599 5'-LTR

1076–2692 gag

1076–6292 gag-pol

5948–5957 splice acceptor site

6232–8229 env ecotropic

8237–8600 pol sequences (NdeI/XbaI)

8322–8331 splice acceptor site

8640–9359 EGFP gene

9422–10014 3'-LTR

The construction scheme for and structure of pGH45 are depicted in FIGS. 1–3.

The viral proviral sequence from the beginning of the 5'-LTR to the 3'-end of env in the plasmid pGH45 corresponds to the wt-sequence as present in pNca. Downstream of the env gene, the sequence contains the 3'-terminal part of the pol gene, the EGFP gene and the 3'-LTR as present in the plasmid pMLM38. The repeated pol sequence containing the splice acceptor site consists in a 0,4 kb fragment spanning from the NdeI site to the XbaI site present in the MOMLV pol gene, comprising SEQ ID NO: 6 or a variant thereof.

A2. Propagation and Transgene Expression

Proviral DNA was transfected into NIH 3T3 cells by calcium phosphate precipitation, and supernatants were drawn 3 days post transfection. Infected NIH 3T3 cells were used for the establishment of producer pools and for repeated infection experiments. The vector displayed substantial EGFP expression and replication as demonstrated by fluorescent focus formation following infection in vitro (FIG. 4) and by induction of syncytia on RatXC cells. The growth properties were assessed in 5 repeated infections on NIH 3T3 cells. Over this 15 days period, propagation remained relatively stable at a level of one to two logs of FFU (Fluorescent focus forming units) per 3 days infection (FIG. 5). The functionality of the construct is an indication of balanced expression of the reporter and the viral proteins. The titer of producer pools as determined by fluorescence microscopy and by FACS analysis (FIG. 6) is about $10^6$ FFU per ml. In infections at low m.o.i., one FFU corresponds to $10^2$ EGFP expressing cells, reflecting the propagation of the vector.

A3 Genetic Stability

Genomic rearrangements leading to wild type (wt) formation are a well known problem with retroviral vectors in general. Especially, with replication competent constructs, loss of transgene expression due to deletions has frequently been observed. The genetic integrity of the vector was therefore followed by PCR. Lysates of the infected cells were subjected to PCR reactions specific for wt arrangements or for the original vector structure, respectively. The detection limit of the assays was below $5 \times 10^3$ copies per reaction. The design of the PCR is depicted in FIG. 7. A first construct, designated GH20, displayed wt-reversion, being detectable yet after three passages. With an improved version of the vector (GH45), after six passages (d21), no wt specific band was detectable in the PCR assay, indicating a low reversion rate. Interestingly, the genomic sequence of the initial construct GH20 is identical to that of GH45, but 150 bp of retroviral sequences are present outside the genomic transcription unit in the GH20 plasmid DNA, directly upstream of the 5'-LTR. As this sequence is excluded from viral replication, homologous DNA recombination during transfection most probably accounts for the observed rearrangements.

A4. Arrestment of the Vector by Targeted Deletion

The duplication of the SA region in the vector resulted in a 0,4 kb tandem repeat, flanking the env gene (FIG. 3). Deletion of genomic sequences due to repeated sequences in the retroviral genome and its application for targeted rearrangements has been described previously. Indeed, in GH20, the loss of the env gene by recombination between the repeats was observed at high frequency. Clones of infected cells were tested for the expected deletion by PCR (data not shown). About 30% (8 out of 28) of the EGFP expressing clones, isolated after three rounds of infection, displayed the env deleted structure in PCR testing. Altering the size of the repeated regions in the genome should provide a means to control the virulence of the vector by targeted destabilization of the viral env gene without negatively affecting the expression of the gene of interest.

DISCUSSION

Retroviral vectors, that are stably expressing a transgene and that are replication competent in mammalians represent -due to a notably enhanced transduction efficiency- a useful tool for delivering polynucleotides to cells, in particular for suicide gene therapy. We attempted a multiple alternative splice approach for the expression of a reporter gene in MOMLV. The efficient translation of the transgene and the propagation of the vector strongly indicate a balanced distribution of the splice products. Of course, variants of the presented vector with alterations in the second splice acceptor region can be constructed in order to improve the effects on splicing and on the arrestment rate by env deletion. Following the genomic stability of the construct by PCR revealed no revertant structures arising during a period of 21 days.

B. Construction and Uses of Semi-replicating Viral Constructs

The general concept is to generate two transcomplementary retroviruses, that each carry a transgene. Both types of retroviral particles are pseudotyped with two different envelopes, so that one single cell can be infected by these two types of transcomplementary retroviral particles: a cell doubly infected will itself produce novel retroviral particles of both types, and so continue the propagation of the transgenes.

B1. Description of <<ying-yang>> Plasmid Construction (See FIG. 8)

The ying-yang plasmids contain the four following expression cassettes (see FIG. no. 8):

Cassette n°1:
- LTR 5' of Mo-MLV (derived from PNCA (Colicelli J. J. Mol. Biol., 1988, 199:47–59)).
- The splice donor site of Mo-MLV
- packaging (v) sequence of Mo-MLV
- The gag-pol coding sequences. However, the pol gene has been deleted at its 3' end at the XbaI site (position of PNCA) and an artificial STOP codon has been added downstream of XbaI site. This deletion, without affecting the activity of pol gene, reduces the possibility of recombination with the env expression cassette. Within the pol gene (upstream of XbaI site), is located the splice acceptor site of Mo-MLV.
- The polynucleotide, which can be a marker gene (like—galactosidase, Enhanced Green Fluorescent Protein) or a therapeutic gene (HSV-TK, cytokines . . . ). The polynucleotide is expressed after splicing of RNA between donor and acceptor site (see upstream).
- 50 base pairs preceding LTR 3' of Mo-MLV and containing the poly-purine tract.
- LTR 3' of Mo-MLV.

Cassette n°2:
- The CMV enhancer and promoter sequences, derived from commercial plasmid pUTSV1 (Cayla, Toulouse).
- The gp 70 coding sequences of feline Rd114 oncornavirus derived from FBRDSALF plasmid (Cosset et al, J. Virol (1995) 69:7430–7436).
- The polyA sequences of SV40 virus.

Cassette n°3:
- LTR 5' of Mo-MLV (derived from PNCA (Colicelli J. J. Mol. Biol., 1988,199:47–59)).
- The splice donor site of Mo-MLV
- The packaging (y) sequence of Mo-MLV with downstream sequences (various lengths possible) which also contributes to the encapsidation efficiency: These downstream sequences contain the beginning of gag: therefore, to prevent the initiation of translation of gag, the ATG of gag has been mutated.
- The env4070A coding sequences.
- The IRES sequence (Internal Ribosomal Entry Sequence) of ECMV, derived from pCITE plasmid (NOVAGEN): this sequence allows the reinitiation of translation.
- The polynucleotide, which can be a marker gene (like □-galactosidase, Enhanced Green Fluorescent Protein) or a therapeutic gene (HSV-TK, cytokines . . . ). The polynucleotide can be the same than in construction no. 1 or can be another one.
- 50 base pairs preceding LTR 3' of Mo-MLV and containing the poly-purine tract.
- LTR 3' of Mo-MLV.

Cassette n°4:
- The CMV enhancer and promoter sequences, derived from commercial plasmid pUTSV1 (Cayla, Toulouse).
- The gag-pol coding sequences of Mo-MLV. The end of pol gene has been deleted at the XbaI Site, as described in cassette n°1.
- The polyA sequences of SV40 virus.

In a particular embodiment, a <<pong>> semi-replicating retroviral plasmid is constructed comprising cassette n°1 and cassette n°2. This creates a so-called plasmovirus. In another embodiment these cassettes n°1 and n°2 can be used in two separate plasmids, which are cotransfected.

Similarly, a <<ping>> semi-replicating retroviral plasmid is constructed comprising cassette n°. 3 and cassette n°. 4. Again, these cassettes n°. 3 and n°. 4 can also be used in two separate plasmids, to be cotransfected.

The pong plasmovirus generates retroviral particles that carry the gag-pol coding sequences, and the pong transgene. At the surface of these pong particles are the Rd114 envelope glycoproteins.

The ping plasmovirus generates retroviral particles that carry the env40707A coding sequences, and the ping transgene. At the surface of these ping particles are the env40707A envelope glycoproteins.

Cells infected by these two types of retroviral particles stably produce new retroviral particles (see FIG. 9): these new retroviral particles are able to transfer either pong viral sequences (containing gag-pol coding sequences, and the pong transgene), or ping viral sequences (containing env40707A coding sequences, and the ping transgene). Retroviral particles generated by these doubly infected cells will then enveloped by env40707 (see FIG. 9). In conclusion this system shall allow an illimited propagation of the polynucleotide (or transgene).

B2. In vitro Experiments

The proof of concept of <<ying-yang>> retroviral plasmids, such as ying-yang plasmoviruses has been made by transfecting cells in vitro, followed by analyzing polynucleotide expression (see FIG. 10). The propagation observed in HCT116 cells successively transfected by ping and pong plasmids is not additive but synergistic, and only ends when nearly 100% of cells can be detected as gfp-positive cells: these cells are named ying-yang cells. What's more, when naive HCT116 cells are infected with supernatant of ying-yang HCT116 cells, the phenomenon of propagation of polynucleotide expression is still observed, resulting in about 100% of positive cells in infected cells. This phenomenon can also be reproduced with the <<supernatant of supernatant>>, i.e. the supernatant of cells infected with the supernatant of ying-yang cells, or the (<<supernatant of supernatant of supernatant>>, . . . (data not shown). These experiments prove that this two viruses-composed system is self-replicative, as predicted. What's more, in the supernatant or in the supernatant of supernatant, the produced retroviral particles are enveloped only with the env40707A. Therefore the propagation of the transgene in cells infected with the supernatant of ying-yang cells can be considered as a "ying-yang effect with a single envelope".

To further characterize this phenomenon, ying-yang HCT116 cells were cloned by limited dilution (see Table 1). Of 40 clones analyzed, 38 were gfp-positive. Of these, 5 were ((double-positive)): the infection of HCT116 cells with the supernatant of these clones induce the propagation of the gfp, until about all cells become gfp-positive.

TABLE 1

Analysis of clones obtained from ying-yang HCT116 cells after limited dilution.

| Number of clones | expression of GFP | Titer (part./ml) | Ping/pong effect |
| --- | --- | --- | --- |
| 5 | + | $10^4$–$5.10^6$ | + |
| 33 | + | − | − |
| 2 | − | − | − |

B3. In Vivo Experiments

The phenomenon of transgene propagation with this ying-yang system was further demonstrated in vivo. A mix of clonal double-positive ying-yang HCT116 cells and naive HCT116 cells was injected into nude mice. As a negative control of propagation, some mice received simple-positive stable ping HCT116 cells. The mice were sacrificed after 3 weeks of tumor growth, and the gfp propagation was analyzed by FACS. While control mix containing stable ping HCT116 cells did not show any propagation, the mix with ying-yang HCT116 cells presented a very high propagation (See table 2). The phenomenon of ying-yang propagation is still observed in these in vivo experiments. This in vivo propagation is further illustrated by the fact that a single injection of supernatant (containing $10^6$ particles) can induce 1% of positive cells in the whole tumor.

TABLE 2

In vivo experiments. $10^7$ HCT116 tumor cells were injected into nude mice. In the case of infection, the supernatant was injected when the tumor was 5 mm large. Mice were sacrificed 3 weeks after the injection of tumor cells, the tumor was digested by collagenase, and live cells sorted by a percoll gradient. Live HCT116 cell were analyzed by FACS for the expression of gfp protein.

| Expt/Results | % positive cells (day 0) | % positive cells (day of sacrifice) |
|---|---|---|
| Mixed cells | | |
| mouse 1 | 0.5% | 10% |
| mouse 2 | 0.5% | 12% |
| mouse 3 | 2% | 20% |
| mouse 4 | 2% | 35% |
| mouse 5 | 20% | 54% |
| Naive cells | | |
| mouse 1 | 0% | 0% |
| mouse 2 | 0% | 0% |
| Infected cells | | |
| mouse 1 | 0% | 0.5% |
| mouse 2 | 0% | 1.5% |
| Control Ping cells | | |
| mouse 1 | 17% | 17% |
| mouse 2 | 17% | 16% |

Conclusion: a highly effective ying-yang effect was observed that propagates the polynucleotide in cells transfected with the ping and pong retroviral constructs. The ying-yang effect observed with the supernatant of ying-yang infected cells can be considered as a "ying-yang effect with a single envelope". This must be due to the fact that cells infected with pong particles do not express any envelope glycoprotein, and can then be reinfected with ping retroviral particles, to form new stable packaging cell.

Some double-positive clonal ying-yang HCT116 cells do not show the presence of any recombined replicated retroviruses as tested by nested PCR, which confirms that the propagation of transgene observed is due to a ying-yang effect.

Of course, the same effect may be obtained using other types of semi-replicating retroviral constructs, such as for instance with:

the use of stable packaging cells that produce ping and pong particles, the use of supernatant containing ping and pong particles, the use of three different envelopes, one for pong plasmids, and the two others for two ping plasmids carrying different envelopes, which should further enhance the propagation, the use of targeted envelope glycoproteins, tissue-specific promoters or chimeric LTR to enhance the efficiency and/or the specificity of expression of the different components.

C. In Vivo Tumor Regression Using Replicating or Semi-replicating Viral Constructs This example confirms the efficacy of the present invention, by illustrating tumor regression in vivo using replicating or semi-replicating viral constructs expressing a thymidine kinase polypeptide. More particularly, packaging cells producing replicative retroviral construct were injected into mice, either in combination with tumor cells or directly into established tumors. Gene transfer was assessed as well as tumor regression (or size) upon administration of a nucleoside analog (e.g., gancyclovir).

Two packaging cell lines were used in these experiments:

classical packaging cells (control) expressing non packageable gag/pol and env genes together with a packageable defective retroviral vector, and thus producing infectious but defective retroviral particles, cells expressing both a packageable replicative wild type retrovirus and a packageable defective retroviral vector (i.e., two transcomplementing retroviral constructs), and thus producing infectious and replicative particles.

C1. Co-injection of Tumor Cells and Packaging Cells

In order to compare the properties of replicative and defective retroviral vectors in a quantitative manner, mixture of DHDK12 tumor cells (98%) and packaging cell lines (2%) producing either replicative or defective retroviral vectors transducing TK/GFP were prepared. 10 millions cells were injected subcutaneously in nude mice (day 0). At day 7, animals were separated in two groups, one receiving ganciclovir (150 mg/kg/jour) for 7 days. Mice were then sacrificed (day 14). The tumors were dissected, weighted, and the percentage of GFP expressing cells was measured after dilaceration by flow cytometry analysis.

The results of this experiment are presented on FIG. 12. These results demonstrate that (i) gene transfer is much more efficient with a replicative than a defective vector as assessed by the proportion of GFP expressing cell in the groups not receiving ganciclovir; (ii) GCV treatment reduces dramatically the number of GFP expressing cells in both groups; (iii) a significant reduction of the tumor volume is only observed in the group receiving the replicative vector and treated with ganciclovir in accordance with the efficiency of transgene transduction. It should be noted that this experiment was performed in nude mice and therefore there is not a full eradication of the tumor which requires a competent immune system.

C2. Injection of Packaging Cells into Established Tumors

Subcutaneous tumors were first generated in nude mice by injection of DHDK12 cells. After 7 days, when the tumors are palpable, they were injected with approximately $3 \times 10^6$ packaging cells releasing either a replicative or a defective retroviral vector transducing TK/GFP. 7 days later, animals were treated or not with ganciclovir for 7 days. Tumor were analysed as for FIG. 12.

The results presented on FIG. 13 show that only replicative vectors lead to a significant transduction of the tumor cells and therapeutic effect.

What is claimed is:

1. A recombinant, replicating retroviral genome, wherein said genome comprises a LTR sequence, a packaging sequence, gag, pol and env coding regions and a foreign polynucleotide, said foreign polynucleotide being inserted in said genome outside of the LTR sequence.

2. A recombinant replicating retroviral genome, wherein said genome comprises a LTR sequence, a packaging sequence, gag, pol and env coding regions and a foreign polynucleotide, said env coding region encoding a modified envelope glycoprotein.

3. A recombinant replicating retroviral genome of claim 1, wherein the polynucleotide is inserted downstream of the env coding region and wherein a splice acceptor site is inserted between said env coding region and said polynucleotide.

4. A recombinant replicating retroviral genome of claim 1, wherein the polynucleotide is under the transcriptional control of a regulated promoter.

5. A recombinant replicating retroviral genome of claim 2, wherein the modified envelope glycoprotein comprises a selected epitope.

6. A recombinant replicating retroviral genome of claim 2, wherein the modified envelope glycoprotein has a modified host range.

7. A recombinant replicating viral construct, wherein said viral construct comprises a LTR sequence, a packaging sequence, gag, pol and env coding regions and a foreign polynucleotide, wherein said LTR sequence is a modified LTR sequence which is active in the presence of an activating polypeptide, and wherein said viral construct comprises a polynucleotide encoding said activating polypeptide.

8. A recombinant replicating viral construct, wherein said construct comprises a LTR sequence, a packaging sequence, gag, pol and env coding regions and a foreign polynucleotide, said polynucleotide encoding αGAL4.

9. A replicating retrovirus, wherein said replicating retrovirus comprises a retroviral genome of claim 1.

10. A plasmid, wherein said plasmid comprises a replicating retroviral genome according to claim 1.

11. A composition comprising a retrovirus of claim 9 or a plasmid of claim 10.

12. A pharmaceutical composition comprising a replicating viral construct or genome of claim 2 or claim 7.

13. A retrovirus packaging cell, comprising, integrated into its genome, a recombinant retroviral genome comprising at least one functional retroviral gene selected from gag, pol and env.

14. A retrovirus packaging cell of claim 13, wherein said retroviral genome is a replicating retroviral genome.

15. A retrovirus packaging cell of claim 13, wherein said retroviral genome is a semi-replicating retroviral genome which comprises functional gag and pol genes and lacks an env gene.

16. A retrovirus packaging cell of claim 13, wherein said retroviral genome is a semi-replicating retroviral genome which comprises functional env gene and lacks gag and pol genes.

17. A retrovirus packaging cell of claim 13, comprising a first and a second retroviral genome, wherein said first retroviral genome is a semi-replicating retroviral genome which comprises functional gag and pol genes and lacks an env gene and said second retroviral genome is a semi-replicating retroviral genome which comprises functional env gene and lacks gag and pol genes.

18. A retrovirus packaging cell of claim 13, wherein said cell is a mammalian cell.

19. A composition comprising a retrovirus packaging cell of claim 13.

20. A retrovirus produced by a retrovirus packaging cell of claim 13.

21. A composition comprising a retrovirus produced by a packaging cell of claim 16 and a retrovirus produced by a packaging cell of claim 16.

22. A composition comprising at least two retroviral constructs, for simultaneous, separated or sequential use, wherein said at least two retroviral constructs transcomplement each other when present in a cell, at least one of said retroviral constructs comprising a polynucleotide of interest.

23. The composition of claim 22, wherein each of the at least two retroviral constructs lacks at least one viral gene selected from gag, pol and env.

24. The composition of claim 22, comprising (i) a replicating retroviral construct and (ii) a retroviral construct lacking functional gag and/or pol and/or env gene, one or both of said retroviral constructs comprising a polynucleotide of interest.

25. The composition of claim 24, wherein the defective retroviral construct (i) lacks functional gag, pol and env genes or (ii) lacks a functional env gene.

26. The composition of claim 22, wherein the polynucleotide is under the transcriptional control of a regulated promoter.

27. The composition of claim 24, wherein the replicating retroviral construct comprises a modified envelope glycoprotein, said envelope comprising a selected epitope or having a modified host range.

28. The composition of claim 24, wherein the replicating retroviral construct comprises a modified LTR region which is active in the presence of an activating polypeptide encoded by the replication-defective viral construct.

29. The composition of claim 22, wherein at least one of said retroviral constructs encodes a polypeptide that renders infected cells sensitive to an immune system of a host organism.

30. The composition of claim 22, wherein said viral constructs comprise, in combination or separately, a polynucleotide encoding αGAL4 and a polynucleotide encoding a cytokine.

31. The composition of claim 22, wherein said retroviral constructs are selected from plasmids, retroviruses and retrovirus packaging cells.

32. Compositions comprising at least two semi-replicating retroviruses, for simultaneous, separated or sequential use, said semi-replicating retroviruses (i) lacking at least one viral gene selected from gag, pol and env, (ii) transcomplementing each other when present in a cell, (iii) comprising a polynucleotide and (iv) having a different envelope glycoprotein.

33. Compositions comprising at least three semi-replicating retroviruses, for simultaneous, separated or sequential use, said semi-replicating retroviruses (i) lacking at least one viral gene selected from gag, pol and env, (ii) transcomplementing each other when present in a cell, (iii) comprising a polynucleotide and (iv) having a different envelope glycoprotein.

34. A method for delivering a polynucleotide to a cell, tissue or organ, in vitro or ex vivo, comprising contacting said cell, tissue or organ with a composition of claim 11.

35. A method of preparing a composition for delivering a polynucleotide to a cell, tissue or organ, in vivo, ex vivo or in vitro comprising contacting said retrovirus or plasmid of claim 11 with said cell, tissue or organ.

36. A retroviral packaging cell of claim 18 wherein said mammalian cell is a rodent cell.

37. A retroviral packaging cell of claim 18 wherein said mammalian cell is a human cell.

38. A method of preparing a composition for delivering a polynucleotide to a cell, tissue or organ, in vivo, ex vivo or in vitro comprising contacting said retrovirus or plasmid of claim 11, ex vivo or in vitro with said cell, tissue or organ.

* * * * *

SEQUENCE LISTING

<160> NUMBER OF SEQ ID NOS: 8

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
ggaccatcct ctag                                                       14

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
ggccgctatt taaatggccg gccttaatta aagtctagag gatggtccac cc             52

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ccgggggtgg accatcctct agactttaat taaggccggc catttaaata gc             52

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
agtaccggga ttaatccatg catctccacc accatactg                            39

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
tatggtctct agacatatgc tatggctcgt actctatagg cttcagc                   47

<210> SEQ ID NO 6
<211> LENGTH: 1100
<212> TYPE: DNA
<213> ORGANISM: Artificial Sequence
<220> FEATURE:
<223> OTHER INFORMATION: Description of Artificial Sequence: Partial
      sequence of pGH45

<400> SEQUENCE: 6

-continued

```
tctaacctag aaaagtctct cacttccctg tctgaagttg tcctacagaa tcgaaggggc    60
ctagacttgt tatttctaaa agaaggaggg ctgtgtgctg ctctaaaaga agaatgttgc   120
ttctatgcgg accacacagg actagtgaga gacagcatgg ccaaattgag agagaggctt   180
aatcagagac agaaactgtt tgagtcaact caaggatggt ttgagggact gtttaacaga   240
tccccttggt ttaccacctt gatatctacc attatgggac ccctcattgt actcctaatg   300
attttgctct tcggaccctg cattcttaat cgattagtcc aatttgttaa agacaggata   360
tcagtggtcc aggctctagt tttgactcaa caatatcacc agctgaagcc tatagagtac   420
gagccatagc atatgagatc ttatatgggg cacccccgcc ccttgtaaac ttccctgacc   480
ctgacatgac aagagttact aacagcccct ctctccaagc tcacttacag gctctctact   540
tagtccagca cgaagtctgg agacctctgg cggcagccta ccaagaacaa ctggaccgac   600
cggtggtacc tcacccttac cgagtcggcg acacagtgtg ggtccgccga caccagacta   660
agaacctaga acctcgctgg aaaggacctt acacagtcct gctgaccacc cccaccgccc   720
tcaaagtaga cggcatcgca gcttggatac acgccgccca cgtgaaggct gccgaccccg   780
ggggtggacc atcctctaga ctttaattaa ggccggccat ttaaatagcg gccgccacca   840
tggtgagcaa gggcgaggag ctgttcaccg gggtggtgcc catcctggtc gagctggacg   900
gcgacgtaaa cggccacaag ttcagcgtgt ccggcgaggg cgagggcgat gccacctacg   960
gcaagctgac cctgaagttc atctgcacca ccggcaagct gcccgtgccc tggcccaccc  1020
tcgtgaccac cctgacctac ggcgtgcagt gcttcagccg ctaccccgac cacatgaagc  1080
agcacgactt cttcaagtcc                                             1100
```

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7

```
aattcaatga agaccccac ctgtaggttt ggcaac                              36
```

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8

```
ctaggttgcc aaacctacag gtggggtctt tcattg                             36
```